(12) United States Patent
Reuss

(10) Patent No.: US 6,711,425 B1
(45) Date of Patent: Mar. 23, 2004

(54) PULSE OXIMETER WITH CALIBRATION STABILIZATION

(75) Inventor: James L. Reuss, Waukesha, WI (US)

(73) Assignee: OB Scientific, Inc., Germantown, WI (US)

(*) Notice: Subject to any disclaimer, the term of this patent is extended or adjusted under 35 U.S.C. 154(b) by 0 days.

(21) Appl. No.: 10/156,480

(22) Filed: May 28, 2002

(51) Int. Cl.[7] ................................................. A61B 5/00
(52) U.S. Cl. ........................ 600/331; 600/323; 600/338
(58) Field of Search ............................... 600/322–323, 600/331, 338

(56) References Cited

U.S. PATENT DOCUMENTS

| | | | |
|---|---|---|---|
| 4,623,248 | A | 11/1986 | Sperinde |
| 4,700,708 | A | 10/1987 | New, Jr. et al. |
| 4,714,341 | A | 12/1987 | Hamaguri et al. |
| 4,938,218 | A | 7/1990 | Goodman et al. |
| 4,975,581 | A | 12/1990 | Robinson et al. |
| 5,188,108 | A | 2/1993 | Secker |
| 5,291,884 | A * | 3/1994 | Heinemann et al. ........ 600/322 |
| 5,299,570 | A | 4/1994 | Hatschek |
| 5,413,100 | A | 5/1995 | Barthelemy et al. |
| 5,421,329 | A | 6/1995 | Casciani et al. |
| 5,425,362 | A | 6/1995 | Siker et al. |
| 5,494,032 | A | 2/1996 | Robinson et al. |
| 5,497,769 | A | 3/1996 | Gratton et al. |
| 5,743,260 | A * | 4/1998 | Chung et al. ................ 600/338 |
| 5,782,237 | A | 7/1998 | Casciani et al. |
| 5,782,756 | A | 7/1998 | Mannheimer |
| 6,064,474 | A | 5/2000 | Lee et al. |
| 6,163,715 | A | 12/2000 | Larsen et al. |
| 6,181,958 | B1 | 1/2001 | Steuer et al. |
| 6,226,540 | B1 | 5/2001 | Bernreuter |
| 6,272,363 | B1 | 8/2001 | Casciani et al. |
| 6,339,715 | B1 | 1/2002 | Bahr et al. |
| 6,421,549 | B1 * | 7/2002 | Jacques ..................... 600/331 |
| 2002/0042558 | A1 * | 4/2002 | Mendelson ................. 600/323 |

FOREIGN PATENT DOCUMENTS

| | | |
|---|---|---|
| EP | 0522674 A2 | 1/1993 |
| WO | WO 00/02483 | 1/2000 |

OTHER PUBLICATIONS

R. Bonner et al., "Model for photon migration in turbid biological media". J. Opt. Soc. Am. A 1987; 4:423–432.

J. Johnson et al., "The effect of caput seccedaneum on oxygen saturation measurements". Br. J. Obs. & Gyn. 1990; 97:493–498.

R. Longini et al., "A note on the theory of back scattering of light by living tissue". IEEE Trans. Biom. Eng. 1968;15:4–10.

P. Mannheimer et al., "Wavelength selection for low saturation pulse oximetry". IEEE Trans. Biom. Eng. 1997; 44:148–158.

P. Mannheimer et al., "Physio–Optical considerations in the design of fetal pulse oximetry sensors". Euro. J. Obs. & Gyn. Repr. Bio. 1997; 72(1):S9–S19.

J. Schmitt, "New methods for whole blood oximetry". Ann. Biomed. Eng. 1998; 14(1):35–52.

(List continued on next page.)

Primary Examiner—Max F. Hindenburg
Assistant Examiner—Matthew Kremer
(74) Attorney, Agent, or Firm—Reinhart Boerner Van Duren s.c.

(57) ABSTRACT

An improved pulse oximeter (sensor and monitor) uses a plurality of wavelengths selected to provide sensitivity to both oxygen saturation and deviations in tissue site characteristic(s) from conditions at calibration. The monitor detects and/or removes the effects of deviations on $SpO_2$ calibration, of particular value in fetal/newborn monitoring.

32 Claims, 10 Drawing Sheets

OTHER PUBLICATIONS

J. Schmitt, "Simple photon diffusion analysis of the effects of multiple scattering on pulse oximetry". IEEE Trans. Biom. Eng. 1991; 38:1194–1203.

B. Seelbach–Gobel et al., "The prediction of fetal acidosis by means of intrapartum fetal pulse oximetry". Am. J. Obs. & Gyn. 1999; 180(1):73–81.

J. Severinghaus et al., "Effect of anemia on pulse oximeter accuracy at low saturations". J. Clin Mon. 1990; 6:85–88.

J. Steinke et al., "Role of Light Scattering in Whole Blood Oximetry". IEEEE Trans. Biom. Eng. 1986; 33(3):294–301.

J. Steinke et al., "Reflectance measurements of hematocrit and oxyhemoglobin". Am. J. Physiol. 1987; 253: (Heart Circ. Physiol. 22): H147–H153.

S. Takatani et al., "Theoretical Analysis of Diffuse Reflectance from a Two–Layer Tissue Model". IEEE Trans. Biom. Eng. 1979; 26:656–664.

G. Weiss et al., "Staatistics of penetration depth of photons re–mitted from irradiated tissue". J. Mod. Opt. 1989; 36:349–359.

* cited by examiner

PULSE OXIMETER WITH CALIBRATION STABILIZATION

BACKGROUND OF THE INVENTION

FIELD OF THE INVENTION

The present invention relates generally to pulse oximetry devices and methods. More particularly, the invention is concerned with an improved pulse oximetry system that corrects calibration shifts due to changes in monitoring site characteristics, particularly variations in blood fraction using calibration stabilization. As a result of the calibration stabilization, oxygen saturation monitoring accuracy and availability are improved. The invention is of particular value when applied in fetal pulse oximetry.

Pulse oximeters are employed in patient clinical practice as well as veterinary practice for assessing the level of oxygenation in the blood of a subject, and are well known in the art. Typically, such devices comprise a sensor with light emitting device(s) (emitter(s)) and associated photodetector(s) (detector(s)), attached to a monitoring device performing signal acquisition, analysis, and display/print and/or functions. One particular example of a pulse oximeter is described in U.S. Pat. No. 6,163,715 B1, issued to Larsen et al., which disclosure is incorporated by reference herein.

The signals (oximetry signals) derived from a pulse oximetry sensor are inversely proportional to the net absorption by nearby tissues of the particular wavelengths of light emitted by the sensor. The net absorption at different wavelengths is dependent upon tissue site characteristics, and includes absorption by skin pigmentation, bloodless components such as bone, non-pulsating blood, especially venous, and pulsating blood, predominantly arterial. The signal corresponding to detected light of a given wavelength is thus composed of a baseline or DC component due to non-pulsating absorption, and a pulsating or AC component related primarily to absorption by arterial blood. It is important to note that the light intensity of a given wavelength reaching the detector, and the path the light takes to get there, are determined not only by absorption properties but also by the scattering of light in tissue.

Pulse oximetry sensors typically operate in transmissive mode, wherein light from the emitters passes through one side of a vascularized tissue to reach a detector(s) on the other side of the tissue. This mode is commonly used in neonatal and adult monitoring on fingertips, earlobes, and so forth. Alternatively, the emitters and detector(s) may be placed near each other in a co-planar fashion on the same tissue surface, forming a single active site on the sensor. The light emitted by the sensor enters the tissue proximal to it and, by backscattering, returns in part to the same tissue surface and to the detector(s) of the sensor. Thus an oximetry sensor can operate in a backscattering mode, also known as reflectance mode. The oximetry signals acquired by backscattering are of lower intensity than those obtained in transmissive mode, making this method more susceptible to interference from various sources.

Pulsations occurring in synchrony with the heart rate are apparent in the oximetry signals. These pulsations result from the increased absorption of light occurring during passage of blood through the arterial system. Because the arterial pulsation is the result of systole in the heart, this rapid increase in absorption (decrease in detected light intensity) is referred to herein as the systolic phase of the signal. The period between systolic phases, characterized by a more gradual decrease in absorption, is herein referred to as the diastolic phase. The high pass filtered oximetry signal is commonly inverted when displayed as a photoplethysmographic waveform (i.e., rising with increasing absorption), emphasizing the similarity to an arterial pressure waveform.

The bulk of oxygen transport in the blood takes place bound to the hemoglobin molecule. The oxygenated ($HbO_2$) and reduced (Hb) forms of hemoglobin have different optical extinction (absorption) curves, but blood's scattering of light is relatively insensitive to oxygen saturation. By choosing appropriate wavelengths of light, the plurality of oximetry signals can be interpreted to yield the percentage of saturation of the hemoglobin molecules with oxygen ($SpO_2$). In the prior art, red and infrared pulsatile amplitudes, scaled by their respective baseline or DC light intensities, are combined in a ratiometric equation based upon the Beer-Lambert model of light absorption by media to yield a ratio R related to $SpO_2$. Most commonly, the red wavelength is nominally around 660 nm, and the infrared wavelength is in the range of 880–940 nm.

The relationship of the ratio R to $SpO_2$ predicted by the Beer-Lambert model is actually a poor fit to empirical data. Therefore, the relationship $SpO_2 = f(R)$ is typically established by calibration of the oximetry system against a standard measurement of arterial oxygen saturation ($SaO_2$). The subjects used to perform such calibration must be hypoxic to some degree, either due to a clinical condition or a laboratory procedure, in order to establish $SpO_2$ accuracy below the typical range of a subject's oxygen saturation. Calibration accommodates the tissue and sensor characteristics, by and large correcting the simplifications resulting from the underlying assumption of a Beer-Lambert model, which disregards the scattering of light by blood and tissue.

One application of this invention is in utero fetal pulse oximetry. The fetal oxygen sensor is inserted in or near the uterus of a mother to noninvasively monitor the condition of a fetus. One particular example of a sensor designed for fetal pulse oximetry is described in U.S. Pat. No. 5,425,362, to Siker et al. incorporated by reference herein. The sensor placement is made through the birth canal to reach a monitoring position on the fetus. This process and its outcome are difficult to satisfactorily visualize, even utilizing intrauterine imaging technologies, such as ultrasound. The fetal oxygen sensor operates in reflectance mode, a method that typically results in lower signal amplitudes, and may be subject to "light shunting", in which emitted light returns to the detector without traversing the vascularized tissue bed. Thus, fetal pulse oximetry represents a challenging scenario for signal acquisition in medical monitoring.

Even with empirical calibration, oximeter performance differs from the Beer-Lambert prediction when the characteristics of the tissue at the monitoring site vary from the characteristics at the time of calibration. Edema, or the presence of significant extracellular fluid, can result in lowered oxygen saturation readings in neonates, as described by Johnson et al., "The effect of caput seccedaneum on oxygen saturation measurements". Br. J. Obs. & Gyn. 1990; 97: 493–498. Inaccuracies are particularly evident in conventional pulse oximeters required to operate in low oxygen saturation ranges, e.g., below 75%. In explaining the effects of edema in clinical monitoring of neonates, Johnson et al. (1990) supra also cited changes in photon path length due to increased red absorption as the explanation for lowered saturations. Severinghaus et al., "Effect of anemia on pulse oximeter accuracy at low saturations". J. Clin Mon.

(1990); 6: 85–88, reported that pulse oximetry underestimated the oxygen saturation of anemic patients.

The purpose of fetal pulse oximetry is to reduce the likelihood of fetal morbidity or mortality related to hypoxia, apparent as acidosis at birth. The typical oxygen saturation level to be monitored in the fetus is below 70%, and thus calibration deviation is a concern. The term "calibration deviation" refers to inaccuracies in oxygen saturation determination by a pulse oximeter specifically due to a change in the calibration, or relationship between a ratio of normalized pulse amplitudes, R, and the $SpO_2$. Furthermore, Seelbach-Gobel et al., "The prediction of fetal acidosis by means of intrapartum fetal pulse oximetry". Am. J. Obs. & Gyn. 1999, 180(1): 73–81, present evidence that the level of fetal oxygen saturation correlating to an acidotic arterial pH level of clinical interest is below 40%. Anemia, exsanguination of blood due to pressure on the sensor, and local perfusion changes can all potentially cause a change in the blood fraction of the tissue being illuminated by the fetal oxygen sensor. Interfering factors such as caput, meconium, and extravasated blood can also cause problems.

More sophisticated models of the behavior of light in living tissue have been formulated by Takatani et al., "Theoretical Analysis of Diffuse Reflectance from a Two-Layer Tissue Model", IEEE Trans. Biom. Eng. 1979, 26: 656–664; Steinke et al., "Role of Light Scattering in Whole Blood Oximerty", IEEE Trans. Biom. Eng. 1986; 33(3): 294–301; Schmitt, "Simple photon diffusion analysis of the effects of multiple scattering on pulse oximetry", IEEE Trans. Biom. Eng. 1991, 38: 1194–1203; and others. Many of these models are based upon photon diffusion theory, drawing upon the earlier work of Longini et al., "A note on the theory of backscattering of light by living tissue", IEEE Trans. Biom. Eng. 1968, 15: 4–10. The effects of light scattering that are not taken into account by the simpler Beer-Lambert model are incorporated to more accurately model the behavior of light in tissue. Photon diffusion models illustrate the dependence of the pulse oximeter's calibration upon sensor design choices such as wavelength and emitter-detector spacing, as well as tissue site characteristics, particularly blood fraction or hemoglobin concentration in tissue.

Empirical calibration is still of value in a pulse oximeter, despite the improved understanding obtained by utilizing a better model. Although an equation relating $SpO_2$ to the ratio R can be obtained, it is dependent on the other tissue site characteristics such as blood fraction, arterial versus venous blood proportion, and hematocrit. It is easier to establish the relationship by empirically measuring oxygen saturation and relating it to the ratio R.

The sensitivity of oximetry to hematocrit was noted by Schmitt, "New methods for whole blood oximetry", Ann. Biomed. Eng. 1986, 14(1): 35–52; and Steinke et al., "Reflectance measurements of hematocrit and oxyhomoglobin", Am. J. Physiol. 1987, 253: (Heart Circ. Physiol. 22); H147–H153. The former worked on in vivo oximetry within an artery, the latter on an in vitro instrument for analysis of blood samples. Both proposed the use of multiple light emitting devices at one isobestic wavelength (approximately 810 nm) with different spacing from the detector to measure the hematocrit. This blood fraction information could then be applied to correct the SaO2 measurement made by the same sensor.

U.S. Pat. No. 6,064,474, to Lee et al. reveals an optical method for obtaining the hematocrit value of an in vitro whole blood sample, utilizing multiple isobestic wavelengths (506 nm and 805 nm) to eliminate the sensitivity of the reading to oxygen saturation level as well as plasma scattering. The use of only isobestic wavelengths substantially simplifies the mathematical treatment, eliminating the need for empirical calibration.

U.S. Pat. No. 6,181,958 B1 to Steuer et al., reveals a system for in vivo determination of hematocrit, but implies an application in pulse oximetry as well. Photon diffusion analysis is performed on a model consisting of whole blood, water, and other tissue, with results substantially similar to Schmitt's (1986). An expression is derived for hematocrit assuming use of an isobestic wavelength (805 nm), and it is suggested that the combination of 805 and 660 is helpful for removing pulse oximetry's dependence on hematocrit, blood volume, and emitter-detector spacing. However, the actual solution requires precise measurement of very small pressure variations in the tissue site, utilizing an integral strain gauge, piezoelectric transducer, or other means.

U.S. Pat. No. 5,421,329 ('329) to Casciani et al. and U.S. Pat. No. 5,782,237, ('237) to Casciani et al. teach using an optimizing technique for selecting wavelength pairs having "good balance" or "correlation" between the product of the absorption and scattering coefficients of each of the wavelength pairs and an optimization for spacing between the emitter and the detector to minimize sensitivity to perturbation induced artifact. Using the photon diffusion model, equations, and coefficients of Schmitt (1991) supra, describing tissue site characteristics, the '237 and '329 patents duplicate Schmitt's method of perturbing the coefficients of one or more tissue site characteristics to predict the resulting calibration deviations, teaching that selecting a longer red wavelength (in the range of 700–790 nm) can reduce the calibration deviation resulting from blood fraction change to an error level considered acceptable by the inventors. The patents ('329 and '237) address the question of reduced blood fraction, and perturbation induced artifact, such as variations in tissue composition, variations in hemoglobin concentration and variations in force applied between the tissue and the sensor. The '237 patent cites Bonner et al., "Model for photon migration in turbid biological media", J. Opt. Soc. Am. A 1987, 4: 423–432; and Weiss et al., "Statistics of penetration depth of photons re-emitted from irradiated tissue", J. Mod. Opt. 1989, 36: 349–359, in "other publications" on the patent. The claims made in the '329 and '237 patents are further described in Mannheimer et al, "Wavelength selection for low saturation pulse oximetry", IEEE Trans. Biom. Eng. 1997, 44: 148–158; and Mannheimer et al, "Physio-Optical considerations in the design of fetal pulse oximetry sensors", Euro. J. Obs. & Gyn. Repr. Bio. 1997, 72 (1): S9–S19.

However, choosing a wavelength which reduces calibration deviation in the available range of about 600–1000 nm invariably results in a reduction of the device's sensitivity to oxygen saturation change. The sensitivity, equivalent to how much the ratio R varies over the full oxygen saturation range of 0–100%, is close to optimal around 660 nm. Also, for oxygen saturations above 80%, the potential error due to calibration deviation may increase for red wavelengths longer than 660 nm (contrast '237 FIG. 8B and FIG. 12B). Apparently, for these reasons, the inventors of '329 and '237 recommended choosing 735 nm only for monitoring lower oxygen saturations, below 70%.

Foreign Patent Document WO 00/02483, to Tobler et al. discloses a means of detecting a change in blood fraction in a fetal pulse oximeter. The patent teaches that the oxygen saturation values may be calculated independently in an oximeter incorporating and calibrated to use several different red wavelengths. If the oxygen saturation values disagree, then the blood fraction has varied from the conditions found during calibration. However, no means is noted for correcting the deviation.

U.S. Pat. No. 5,413,100, to Barthelemy et al. discloses a method for correcting oxygen saturation measurement in the presence of carbon monoxide, teaching the use of 660, 750 and 940 nm wavelengths in a pulse oximetry sensor. The measurements from the three wavelengths are combined in a system of simultaneous linear equations to solve for the fraction of hemoglobin bound to carbon monoxide, as well as the fractions of oxygenated and reduced hemoglobin. This pulse oximeter is still susceptible to calibration deviation resulting from perturbations in tissue site characteristics.

A need therefore remains for an oximetry system in which calibration is stabilized without sacrificing sensitivity to oxygen saturation. This is especially true in the challenging domain of fetal pulse oximetry. Furthermore, for convenience it is desirable after birth to continue monitoring with the same oxygen sensor employed in utero, although the newborn's oxygen saturation may rapidly rise above 70%. Lastly, it is preferable to further reduce the errors in oxygen saturation resulting from calibration deviation, and potentially identify and correct deviations caused by a broader range of non-ideal tissue site characteristics.

SUMMARY OF THE INVENTION

It is therefore an object of the invention to provide a pulse oximetry system with the capability of quantifying and/or eliminating the calibration deviation resulting from changes in tissue site characteristics in the pulse oximetry signals.

It is yet another object of the invention to provide a pulse oximetry system in which calibration stability can be achieved without sacrificing sensitivity to oxygen saturation changes.

It is still another object of the invention to provide a pulse oximetry system in which calibration stability and sensitivity to oxygen saturation change can both be achieved over the full oxygen saturation range for the subject.

It is yet another object of the invention to provide a pulse oximetry system with the aforementioned advantages suitable for monitoring a fetus while in utero, as well as after birth.

In one preferred embodiment of the invention, the pulse oximeter system comprises a monitor and an oxygen sensor comprising emitter(s) creating a plurality of incident light wavelengths, plus one or more light detector(s), providing signals corresponding to light returned from the tissue near the sensor after exposure to the incident light wavelengths, the system being designed to quantify and/or correct calibration deviation(s).

In another preferred embodiment of the invention, the wavelengths emitted by the oxygen sensor are chosen such that (a) at least one combination of wavelengths (a ratio wavelength set) possesses high sensitivity to blood oxygen saturation changes, and (b) at least two wavelengths (a correction wavelength set), of which at least one wavelength is not already employed in the ratio wavelength set, exhibit substantially different dependence upon a tissue site characteristic other than blood oxygen saturation.

In still another preferred embodiment of the invention, the monitor processes the signal data acquired for each wavelength in order to recalculate the signals of the ratio wavelength set, based upon both a (possibly perturbed) signal data of the ratio wavelength set, and a (possibly perturbed) signal data of the correction wavelength set.

In yet another preferred embodiment of the invention, the wavelengths of the oxygen sensor are chosen so that the calibration deviation resulting from changes in multiple tissue site characteristics can be quantified and/or corrected by employing multiple correction wavelength sets.

In another preferred embodiment of the invention, the monitor determines which correction wavelength set(s), if any, to employ in recalculating the signal data corresponding to the ratio wavelength set, based upon an estimate of the blood oxygen saturation level derived from the (possibly perturbed) signal data corresponding to the ratio wavelength set.

In still another preferred embodiment of the invention, the monitor determines which correction wavelength set(s), if any, to employ in recalculating the signal data corresponding to ratio wavelength set, based upon a pattern of a magnitude (s) and direction(s) of deviation(s) in signal data corresponding to a correction wavelength set from the expected mathematical relationships between members of each set.

Other advantages and features of the invention, together with the organization and manner of operation thereof, will become apparent from the following detailed description when taken in conjunction with the accompanying drawings wherein like elements have like numerals throughout the drawings. It is expressly understood that the drawings are for the purpose of illustration and description only, and are not intended as a definition of the limits of the invention.

DETAILED DESCRIPTION OF THE PREFERRED EMBODIMENTS

Figure 1:
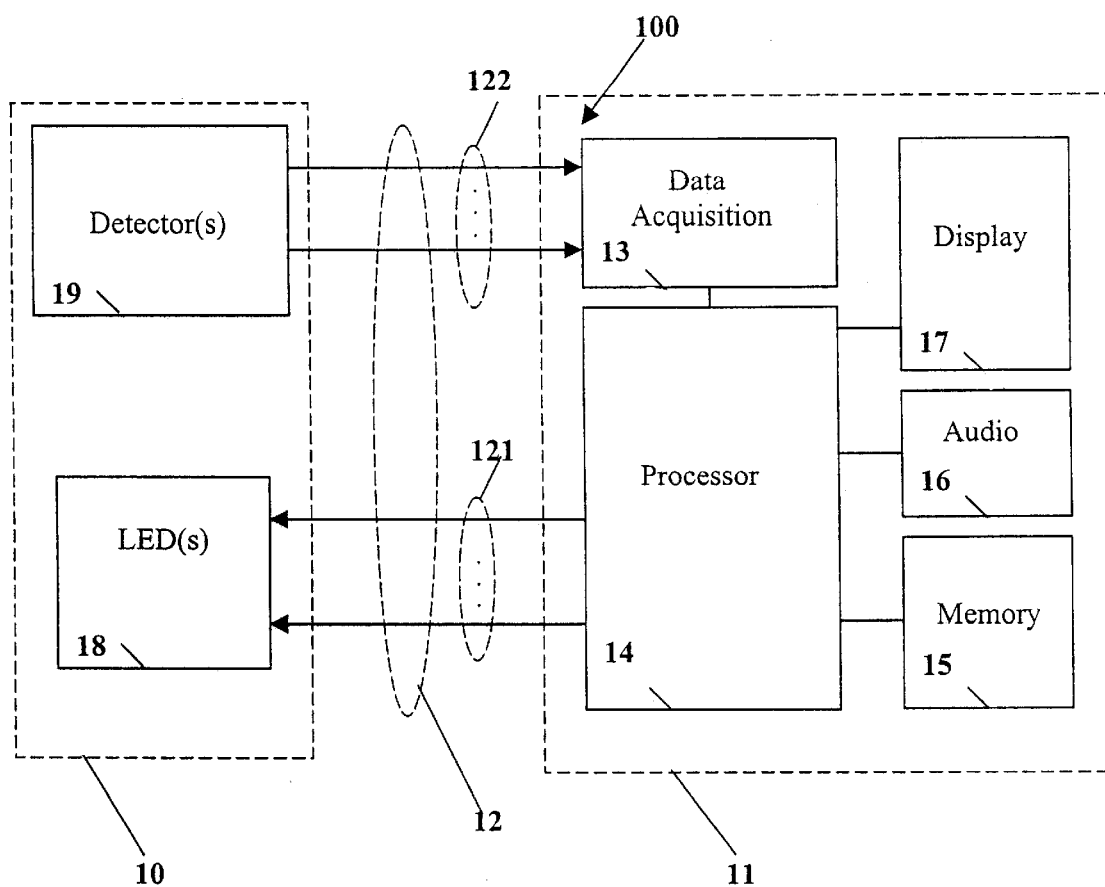
FIG. 1 is a block diagram of a pulse oximetry system constructed in accordance with one embodiment of the present invention.

Before one embodiment of the invention is explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items. The use of "consisting of" and variations thereof herein is meant to encompass only the items listed thereafter. The use of a letter to identify steps of a method or process is simply for identification and is not meant to indicate that the steps should be performed in a particular order.

In the present invention, pulse oximetry is made safer and more accurate by quantifying and/or correcting the signal data to stabilize the calibration despite changes in tissue site characteristics and/or structure. The description is divided into an overview of the pulse oximetry system, the calibration stabilization process, and wavelength selection.

OVERVIEW OF THE PULSE OXIMETRY SYSTEM

A pulse oximeter (herein also "pulse oximetry system") 100 built in accordance with an embodiment of this invention is illustrated in FIG. 1, consisting of a sensor (herein also "oxygen sensor" or "sensor device") 10 and monitor unit (herein also "monitor" or "monitor device") 11 connected by wiring 12 carrying control signals and detector signals. One example of an oximeter constructed in accordance with the block diagram of FIG. 1 is disclosed in the U.S. Pat. No. 6,163,715 to Larsen et al., which disclosure is incorporated by reference.

The sensor (herein also "sensor device") 10 comprising a plurality of light emitting device(s) 18 and detector(s) 19 is initially coupled to blood-carrying tissue. In some applications, the light emitting devices 18, typically light-emitting diodes (LEDs), are directed at the tissue, and the detector(s) 19 are positioned on the opposite side of the tissue to determine the amount of absorbed light. Such a transmissive mode arrangement can, for example, be made through a finger or an ear lobe. Alternatively, rather than detecting light transmitted through the tissue site, a reflectance mode arrangement is used where the detector(s) 19 and the emitting device(s) 18 are on the same side of the tissue. The detector(s) 19 receive a portion of the light from the light emitting device(s) 18 which has scattered back to the surface from the tissue beneath the sensor.

Figure 2:
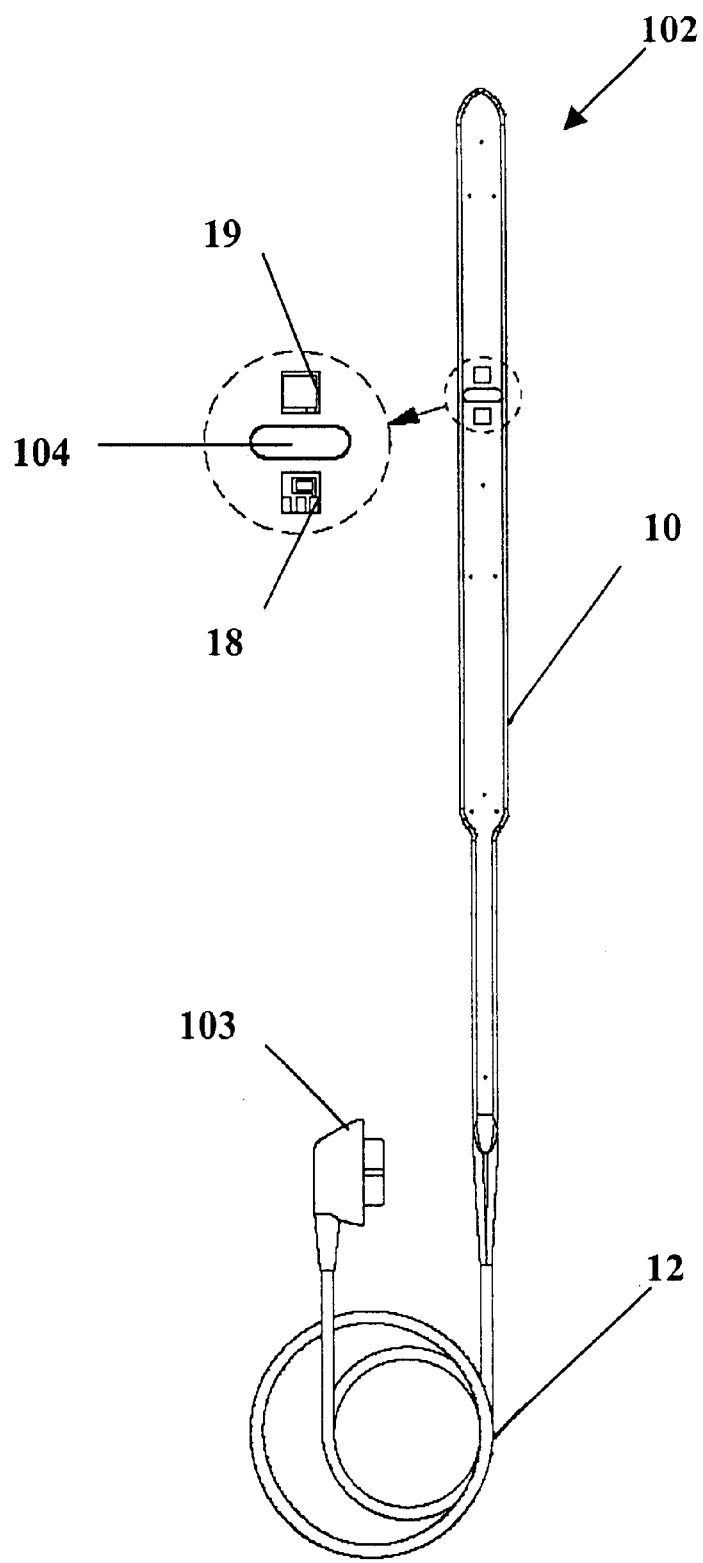
FIG. 2 is a schematic diagram for a reflectance mode pulse oximetry sensor constructed in accordance with one embodiment of the present invention.

A fetal pulse oximetry sensor 102 built in accordance with an embodiment of this invention in shown in FIG. 2 has a sensor 10 with a plurality of light emitting device(s) 18 and detectors 19, wiring 12 and a monitor connector 103, for connecting to monitor unit 11 (shown in FIG. 1). A light blocker 104 is situated between the light emitting device(s) 18 and the detector(s) 19 in order to prevent light from traveling through the body of the sensor without entering the tissue being monitored. In the case of fetal oximetry, as noted above, the sensor 10 is inserted into or near the uterus of a mother to non-invasively monitor the condition of a fetus. This particular configuration of fetal sensor is designed to operate in reflectance mode. It will be noted that the distance from the detector 19 to any of the light emitting devices(s) 18 is equal to the distance from the detector 19 to any of the other light emitting device(s) 18.

Referring now to FIG. 1, control signals are directed from the processing circuit 14 to the light emitting device(s) 18 via control lines 121. The data acquisition circuitry 13 receives the detector signal(s) 122 from the photodetector(s) 19. In a typical configuration, the narrow-band light emitting device(s) 18 are sequentially illuminated in multiplexed fashion so that the tissue is exposed to only one of each frequency band corresponding to light emitting device 18 at a time. A single broad-band photodetector 19 can then be employed, and the detector signal 122 represents the time-multiplexed light intensity of each emitter frequency band.

The detector signal(s) 122 are demultiplexed through analog or digital signal processing in the monitor unit 11 to obtain input signals 21. Preferably, the input signal(s) 21 are initially conditioned to remove noise, due to ambient light, fluctuations on the input power line, drift, and high frequency interference. Other filters, for removing noise due to motion artifacts, or other sources, are also possible. As noted above, since noise is particularly acute in reflectance-based oximetry, noise removal steps are particularly important in fetal oximetry. Upon completion of the signal processing steps, the resultant signals can also be visually displayed, printed, and/or converted to an audible representation.

Figure 4:
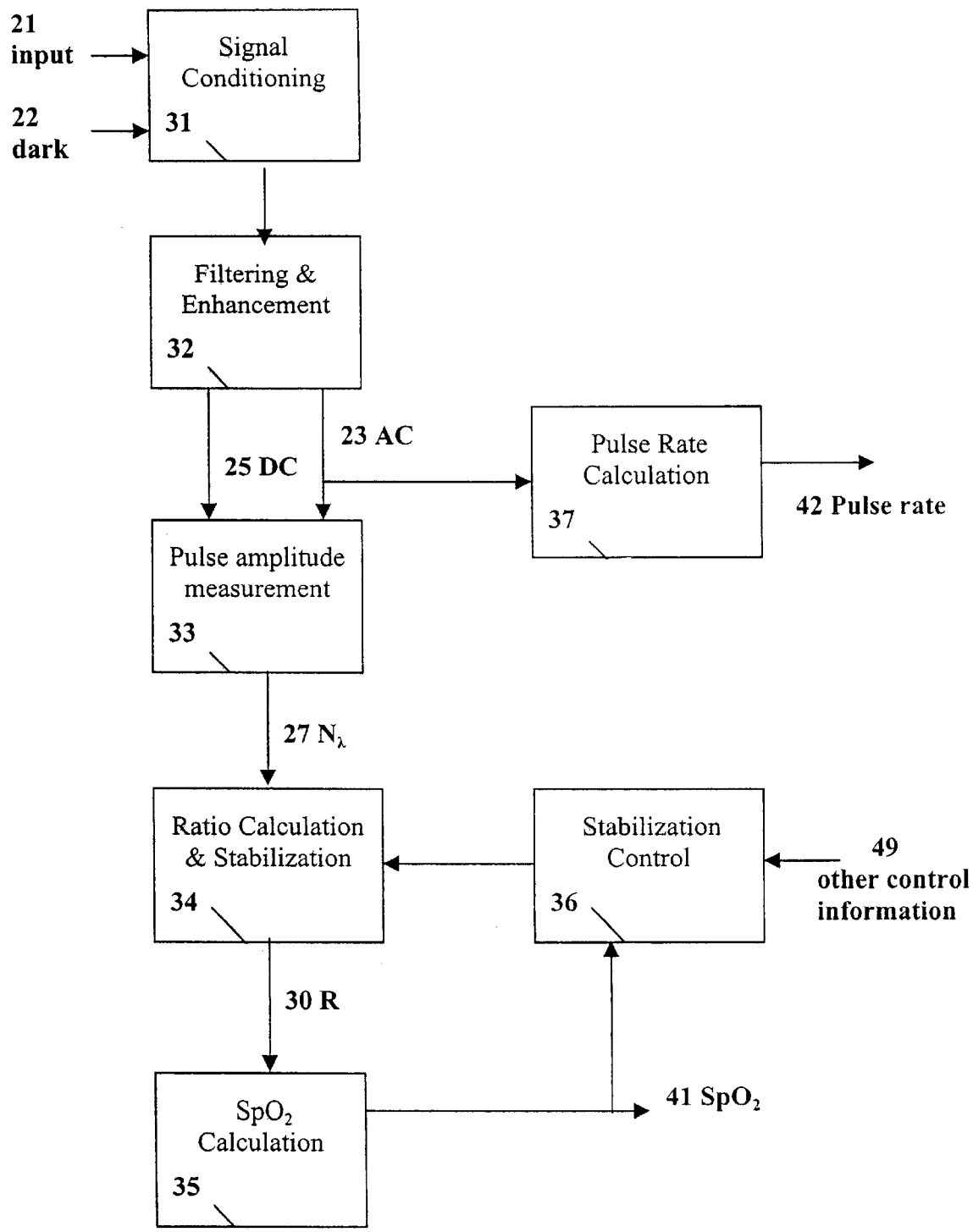
FIG. 4 is a diagram of the signal data flow in an enhanced pulse oximeter in accordance with one embodiment of the invention.

The monitor unit (herein also "monitor device") 11 contains various components schematically indicated here, including data acquisition circuitry (herein also "data acquisition component") 13, processing capability (herein also "processor" or "processing circuit" or "computing component") 14, memory circuitry (herein also "memory storage component") 15, audio signal output 16, and visual display plus keypad or other operator controls (herein also "visual presentation component") 17. Advantageously the monitor device 11 in the present invention has, in the computing component, the capability for oxygen saturation determination with calibration stabilization for quantifying and/or correcting and/or eliminating a calibration deviation (s) resulting from changes in tissue site characteristics in a pulse oximetry signal. Generally, the processing circuitry 14 drives the light emitting devices 18 and processes received signals from the detector(s) 19 to calculate blood oxygenation $SpO_2$ or other physiological parameters. The data acquisition circuitry 13 digitizes the analog signal for use by the processing circuitry 14, and, in some cases, may provide analog processing of analog signals. The calibration stabilization process used in the monitor device occurs in the stabilization step 34 of the signal processing, as shown in FIG. 4, as will be described in detail.

As is known in the art, variations of this design, relating to the number, location, type, and emission frequency bands of the light emitting device(s); control signal characteristics, multiplexing frequencies and schemes; number and type of photodetector(s), and their optical passbands; method of transfer of the signals between sensor and monitor (electrical wiring or fiberoptics); intended use of the sensor at different tissue sites; features of the monitor unit including variations in signal processing techniques; packaging of the sensor or monitor components; processing in embedded versus general-purpose computing devices; distribution of components over a network, etc., may be made. These variations do not change the fundamental principles and limitations of pulse oximeters as addressed by this invention.

In the typical configuration disclosed herein, the multiplexing frequency for the sequential illumination of the light emitting device(s) 18 is chosen well above the Nyquist frequency for the inherent frequency content of the plethysmographic signals (approximately 0–20 Hz), and high enough such that the phase lag between data corresponding to each light emitting device is relatively small. In the preferred embodiment, multiplexing takes place at 600 iterations/sec, meeting both of these requirements.

Figure 3:
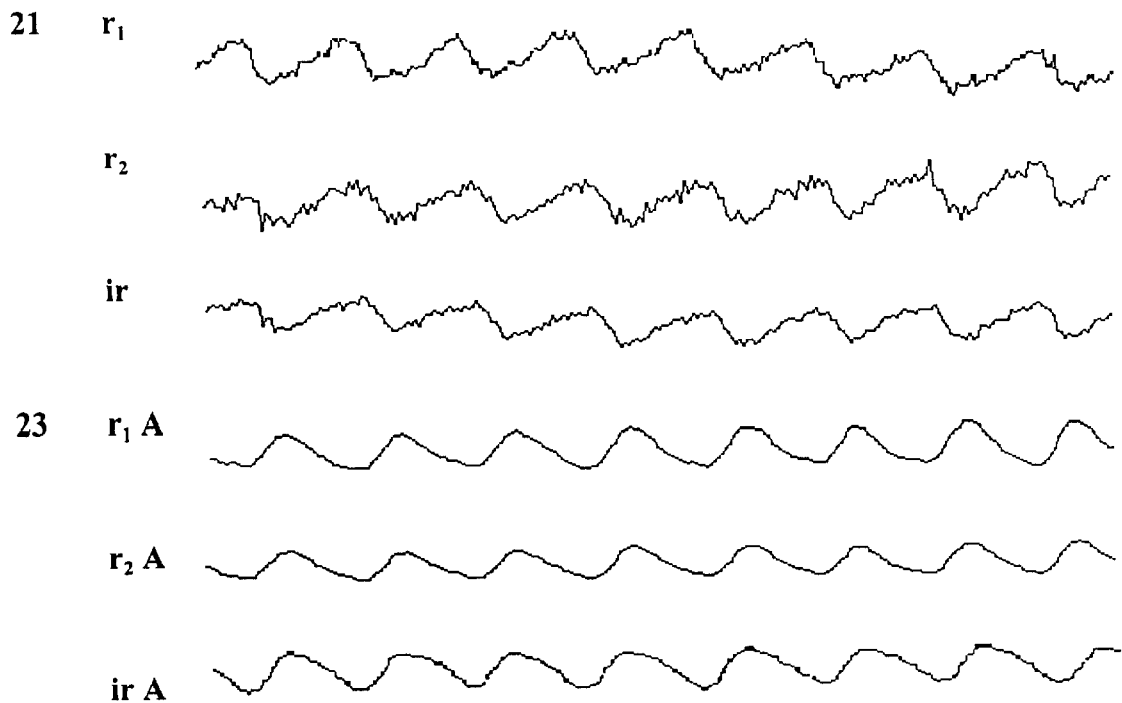
FIG. 3 is a representative sample of various fetal oximetry signals obtained by an enhanced pulse oximeter in accordance with one embodiment of the invention.

In FIG. 3, the resulting demultiplexed input signals 21 each represent transmissivity of light of a particular frequency band through the tissue site. The signals will drop during cardiac systole as a result of increased absorption of light by the bolus of arterial blood passing through the site. Three demultiplexed signals 21 are illustrated in FIG. 3 and labeled $r_1$, $r_2$ and ir.

The input signals from the sensot may be affected by common-mode noise. For example, if the photodetector(s) of the sensor are exposed to ambient light, the additive noise can add a common-mode bias to the oximetry signals, as well as a range of frequencies depending upon the light source. Electromagnetic interference (EMI) can also affect the signals at the sensor, in the sensor cabling, or in the monitor itself, usually modulated by the frequency of line power and/or artificial lighting systems in the environment. Removal of this type of interference occurs, in the preferred embodiment, in the processor 14 after the input signals are converted to the digital domain. However, filtering of noise may also be performed completely or partially in the analog domain, that is, in the data acquisition component 13, without changing the fundamental intention of the step, e.g. the filtering of common mode noise.

The overall flow of signal processing in an enhanced pulse oximeter is shown in FIG. 4, and consists of seven principle steps, steps 31–37. The steps are: step 31 signal conditioning, step 32 filtering and enhancement, step 33 pulse amplitude measurement, step 34 ratio calculation and stabilization which provide the information needed to perform, step 35 SpO2 calculation, and step 37 pulse rate calculation, with step 36 stabilization control, if necessary. In the preferred embodiment, a "dark" signal 22 is acquired from the sensor 10 by sampling the photodetector(s) in the absence of intentionally applied light from the light emitting device(s) 18. The amplitude of this dark signal is tested to detect DC common mode noise, including impinging (and potentially interfering) ambient light. If the level of dark signal is too high, such that the measurement of returning light from the emitter may be impossible due to saturation of the electronics, it may be necessary to disable the oximetry system and alert the operator that the sensor must be repositioned. If the dark signal is at a moderate level, the bias it introduces in the oximetry signals may be eliminated by subtracting the dark signal from each of the input signals 21 in a signal conditioning step 31. In conventional adult or neonatal pulse oximetry, a dark signal less than 50% of the DC level of the returning light from the emitter may be considered moderate; in fetal monitoring, a much lower level (e.g., 10%) would be tolerated due to the intrauterine location of the sensor. If the subtraction is performed on a sample-by-sample basis, as in the preferred embodiment, then noise components in the frequency range of physiological signals may be eliminated from each of the input signals 21.

As noted above, common mode noise is often modulated at the line power frequency. In the preferred embodiment, line frequency rejection is performed in the signal conditioning step 31 utilizing a very simple but effective notch filter. The sampling rate is set to twice the fundamental frequency of line noise. Pairs of samples are then added, resulting in reduction of the sampling rate to the line frequency rate. Utilizing the trigonometric identity $\sin(\theta) = -\sin(\theta+\pi)$, the result of this operation is counter-phase cancellation of the predominantly sinusoidal line noise with minimal processing. In a given locality, the line power frequency has a nominal rating, typically 50 Hz or 60 Hz; however, in some localities the actual frequency can drift considerably around the nominal value. The sampling rate can be established most effectively by characterizing the line frequency dynamically, for example, with a detector in the line power supply, thereby setting the sampling rate. The resulting samples at line frequency rate can later be resampled to a computationally more convenient rate. It will be apparent to those of ordinary skill in the art that other types of line filters can also be used without departing from the invention.

After the signal conditioning step 31, the filtering and enhancement step 32 using band pass filtering is performed to isolate a pulsatile (or "AC") signal 23 corresponding to each input signal 21. Three pulsatile signals 23 are illustrated in FIG. 3 and labeled $r_1$ AC, $r_2$ AC, and ir AC. Each input signal 21 is also lowpass filtered to yield a stable baseline (or "DC") signal 25 essentially free of pulsatility, and relatively noise-free. As seen in FIG. 3, the polarity of the pulsatile signals 23 has been reversed with respect to the input signals 21. That is, systole is now marked by a rise in the enhanced signals. This inversion is frequently performed prior to visual display of the plethysmographic signal, but is not required for algorithmic interpretation of the signals.

The signal conditioning step 31 occurs, in the preferred embodiment, in the processor 14 after the input signals 21 are converted to the digital domain. However, band pass filtering 32 may occur completely or partially in the analog domain, that is, in the data acquisition component 13, without changing the fundamental intention of the step, e.g. band pass filtering. Further, various alternative implementations for signal conditioning suggested in the prior art, such as adaptive filtering, may also be used in the signal conditioning step 31.

The pulsatile 23 and baseline 25 components of the input signals 21 are used in the pulse amplitude measurement step 33, consisting of pulse characterization using identification, qualification, and measurement of pulses in the input. Each qualified pulse identified in the input results in a set of normalized pulse amplitude values $\{N_\lambda\}$ 27, with one measurement in the set corresponding to each wavelength of light from emitter(s) 18. The prior art reveals alternative techniques for determining normalized pulse amplitudes, including natural log transformations, continuous RMS comparisons between the signals, etc., which do not change the fundamental purpose of the step. Averaging, outlier rejection, and other known in the art techniques are applied to the succession of pulse amplitude measurements to increase the accuracy and availability of the derived $SpO_2$ value.

The normalized pulse amplitude values 27 are used in the ratio calculation and stabilization step 34 to give a ratio R 30 of normalized pulse amplitudes at two wavelengths. The wavelengths are called a ratio wavelength set. According to a preferred embodiment of the invention, the pulse amplitude data may be utilized to stabilize the calibration of the ratio value, R, in a calibration stabilization process described below. The calibration stabilization process in step 34 of the present invention is selected and tuned by a calibration control step 36 (also called "Stabilization Control"), based upon the trend of recent $SpO_2$ 41 and other information 49. The control step 36 may, for example, enable calibration stabilization automatically, e.g. if the oxygen saturation trend is below a threshold such as 70%; or calibration stabilization may be manually selected by an operator based upon information about the subject, such as presence of anemia. The control step 36 may also utilize information about the type of sensor 10, i.e., what application the sensor 10 is designed for (adult, neonatal or fetal) and what monitoring site (finger, forehead, fetal back) is used. This information may be determined directly by the monitor unit 11 in the course of reading a memory component embedded in the sensor 10 or connector 103.

After the ratio calculation and stabilization step 34 (if necessary) has been performed, the resulting ratio R 30 is utilized in the oxygen saturation calculation "$SpO_2$ Calculation" step 35 to give the $SpO_2$ value 41. The pulsatile signals are also used in a pulse rate calculation step 37 to yield the pulse rate 42. The algorithms in steps 35 and 37 are designed to derive the $SpO_2$ percentage and pulse rate from the signals over a broad range of physiological conditions and possibly in the presence of interfering factors such as motion. The prior art contains many references to alternative implementations for these algorithms. One example of an oximeter incorporating algorithms is disclosed in the U.S. Pat. No. 6,163,715, supra. In the preferred embodiment, pulse detection and qualification is performed in the pulse characterization step 33 to choose pulses suitable for use in the pulse rate and oxygen saturation calculations.

As described in U.S. Pat. No. 6,339,715 to Bahr et al, the location of a spectral peak in the input signals corresponding to the fundamental cardiac period may also be employed to calculate or confirm the pulse rate.

CALIBRATION STABILIZATION PROCESS

The calibration stabilization process of the present invention used in step 34 is a process by which properly selected wavelengths of light (the correction wavelength set) may be utilized to reduce the calibration deviation resulting from a change in tissue site characteristics. The particular example chosen to illustrate calibration deviation is blood volume change, however the calibration stabilization process of the present invention may be used for other changes in tissue site characteristics, such as, but not limited to hematocrit variation.

The mathematical formulation of photon diffusion analysis as it applies to reflectance mode pulse oximetry as presented by Schmitt (1991) is incorporated by reference herein and assumed herein unless otherwise noted. With certain assumptions of emitter-detector spacing and tissue geometry, as revealed by Schmitt supra, photon diffusion model analysis yields an approximation of $$R = \frac{\Delta I_r / I_r}{\Delta I_{ir} / I_{ir}} = \frac{n_r}{n_{ir}} \approx \frac{S_r K_r(\alpha_r, s) A_r}{S_{ir} K_{ir}(\alpha_{ir}, s) A_{ir}} \quad (1)$$

where $$K_\lambda(\alpha_\lambda, s) \approx \frac{-s^2}{(1 + \alpha_\lambda s)} \quad (2)$$

and

| | |
|---|---|
| R | ratio of normalized red/infrared (arterial) pulse amplitudes |
| λ | a given wavelength of light |
| $I_\lambda$ | intensity of detected light at wavelength λ |
| $\Delta I_\lambda$ | change in $I_\lambda$ |
| $n_\lambda$ | normalized change in $I_\lambda$ |
| $S_\lambda$ | total tissue light scattering at wavelength λ |
| $\alpha_\lambda$ | light attenuation by tissue at wavelength λ |
| s | emitter-detector spacing in sensor geometry |

-continued

| | |
|---|---|
| $K_\lambda$ | dependence on attenuation at wavelength λ and spacing s (reflectance mode geometry) |
| $A_\lambda$ | absorption coefficient of arterial blood at wavelength λ |

The subscripts "r" and "ir" are used to denote particular wavelengths in the red range (below approximately 800 nm) and infrared range (above approximately 800 nm), as conventionally employed in prior art pulse oximetry. Thus the ratio wavelength set is {r, ir}. Although the form of $K_\lambda$ is specific to reflectance mode geometry, it is understood that the invention may also be applied to transmissive mode sensor geometry without departing from the invention in its broadest aspects.

Relating equation (1) to pulse oximetry practice, $A_\lambda$ (as defined in Schmitt (1991) supra equation (2)) is a function of $SaO_2$, representing as it does contributions of oxygenated and reduced hemoglobin. After substituting for $A_\lambda$, equation (1) can be rearranged to obtain $SpO_2$ in terms of R, a relationship analogous to the empirical calibration typically utilized in pulse oximetry. The attenuation coefficients contain dependencies upon overall tissue scattering and absorption properties, which are in turn dependent upon blood fraction, arterial versus venous proportion, and hematocrit (see Schmitt (1991) supra). As illustrated by Schmitt (1991) supra, the R to $SpO_2$ relationship predicted by photon diffusion analysis is a better match to the empirical calibration curves of pulse oximetry than the Beers-Lambert law model provided. This is key to the further development of the invention, in which it is assumed that the empirically derived equivalents of nit can be mathematically corrected according to predictions based on equations (1–2).

Figure 5:
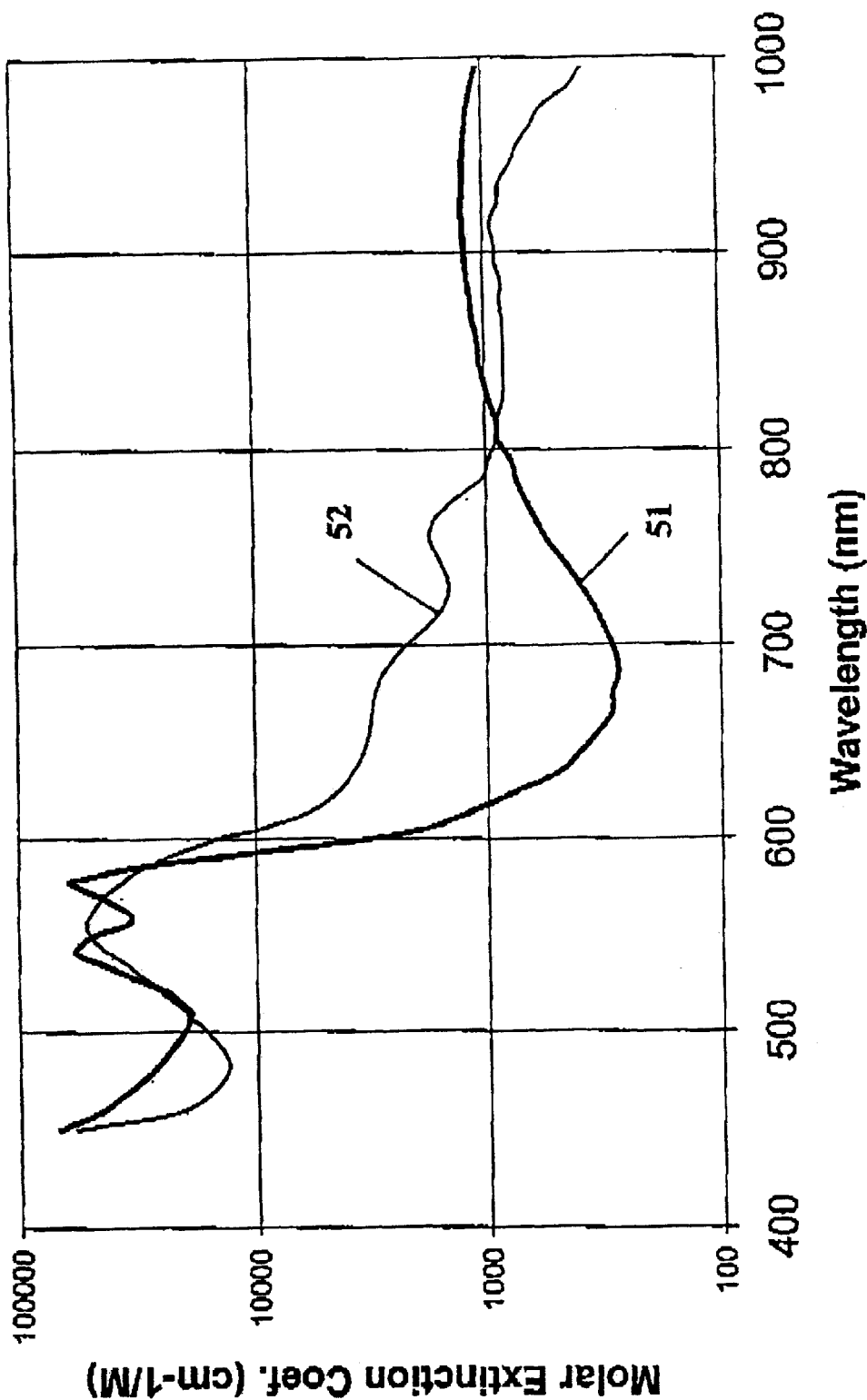
FIG. 5 is a graph of extinction curves for oxygenated and reduced hemoglobin drawn from prior art data.

Equations (1) and (2) were combined with empirical blood and tissue absorption and scattering data for various wavelengths from 600 to 1000 nm to build a computer model of pulse oximetry behavior. FIG. 5 contains extinction curves of 450–1000 nm light for oxygenated hemoglobin 51 and reduced 52 hemoglobin, calculated from data published by Takatani et al. (1979) supra. Four ranges are of particular note: the red wavelengths of approximately 650–699 nm; the longer red wavelengths of 700–799 nm; the near-isobestic wavelengths of 800–815 nm; and the infrared wavelengths of 850–950 nm.

Figure 6:
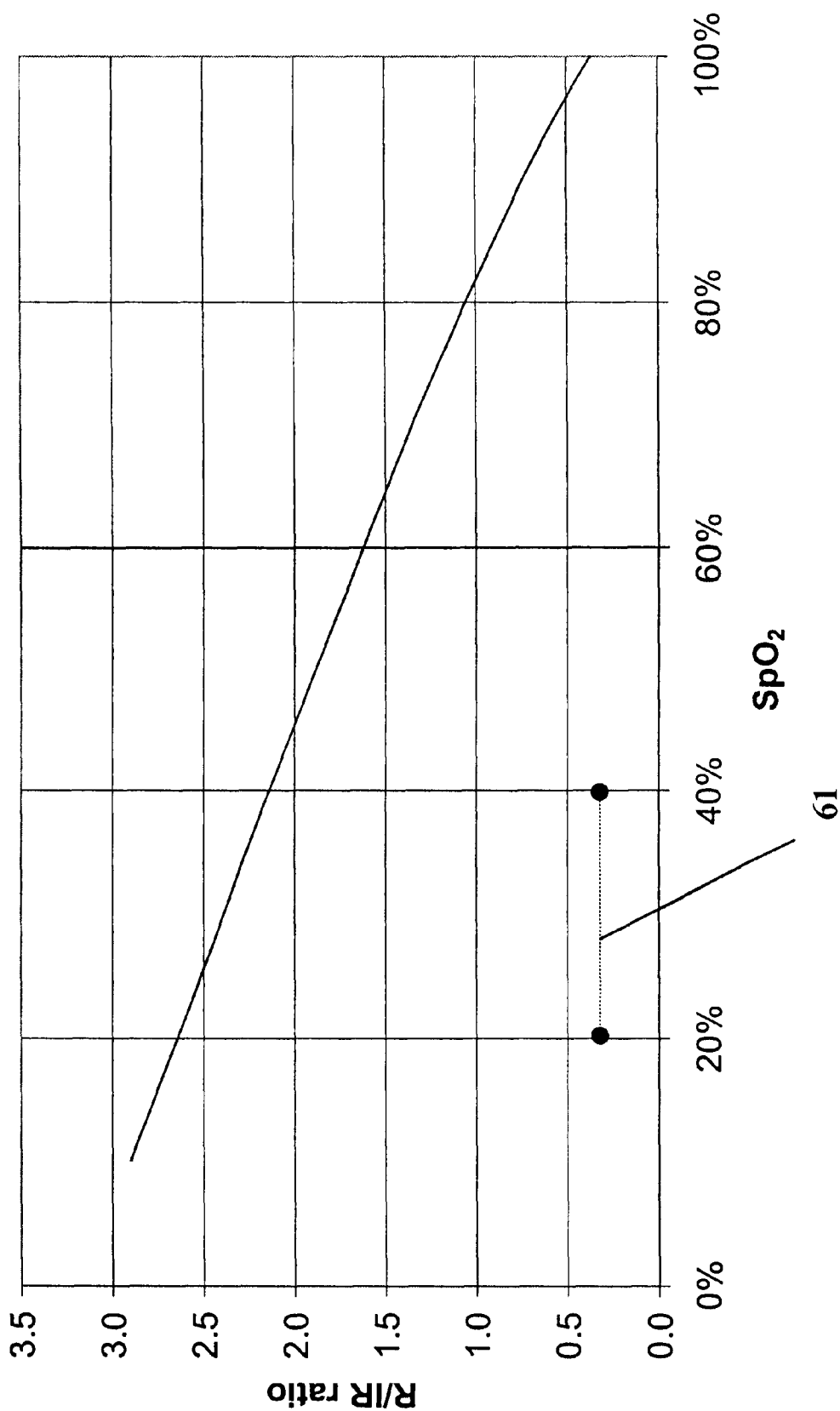
FIG. 6 is a sample calibration curve relating the red/IR ratio R to $SpO_2$, with changes predicted due to increased and decreased blood volume fraction.
Figure 7:
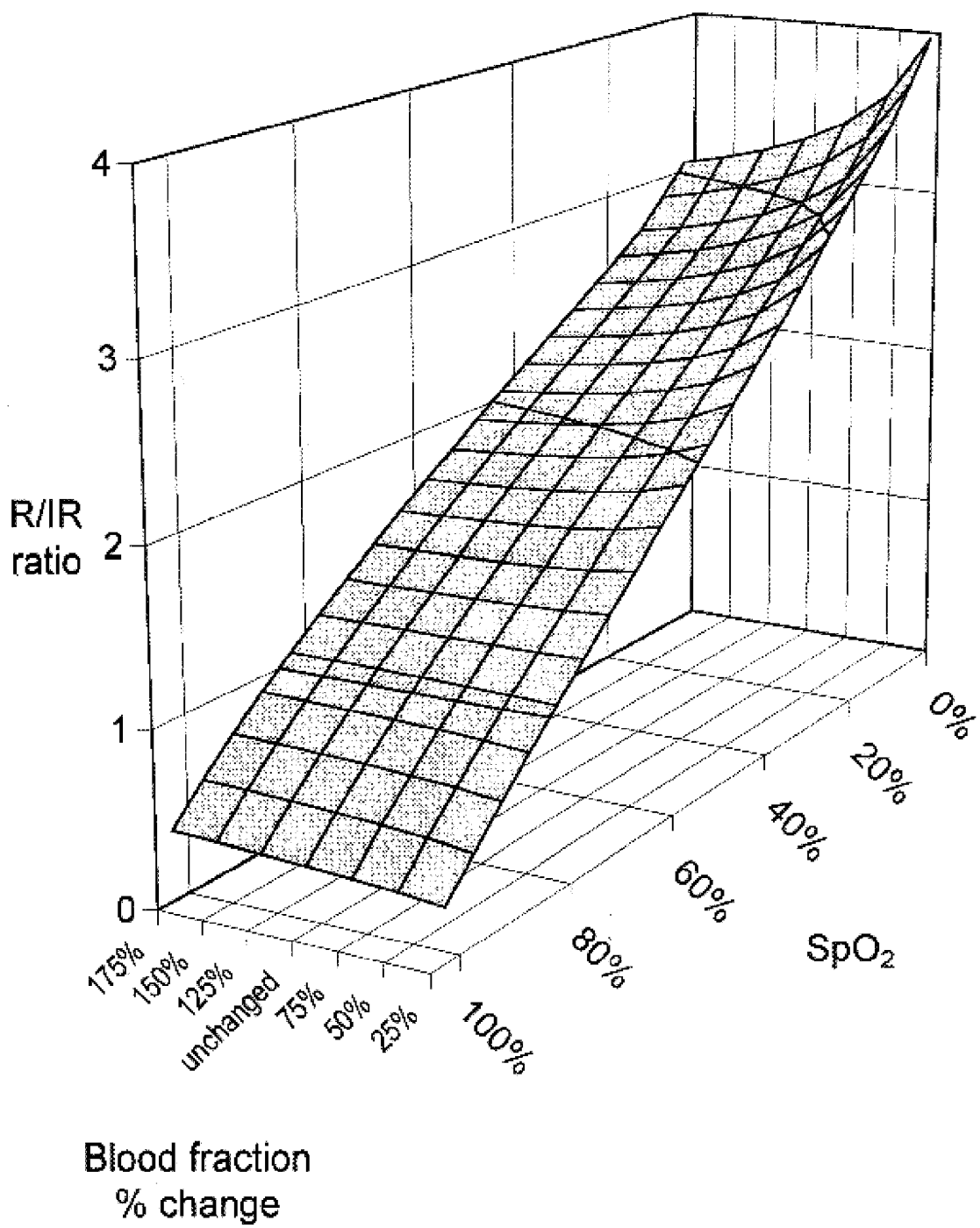
FIG. 7 is a calibration surface relating the red/IR ratio R to blood fraction and $SpO_2$, corresponding to the calibration curve of FIG. 6.

The predicted relationship of the red/infrared ratio R to the $SpO_2$ value for the ratio wavelength set {r, ir}={660 nm, 890 nm} is shown in FIG. 6. In FIGS. 6 and 7, the red/infrared ratio R 30 is labeled "R/IR ratio". These results correspond to a reflectance mode emitter-detector spacing of 14 mm, nominal blood fraction of 1.25% arterial blood and 3.75% venous blood for a total of 5% blood in the tissue, and hematocrit of 45. However, other assumptions about sensor geometry and ideal tissue site characteristics could be made without departing from the invention in its broadest aspects.

Figure 8:
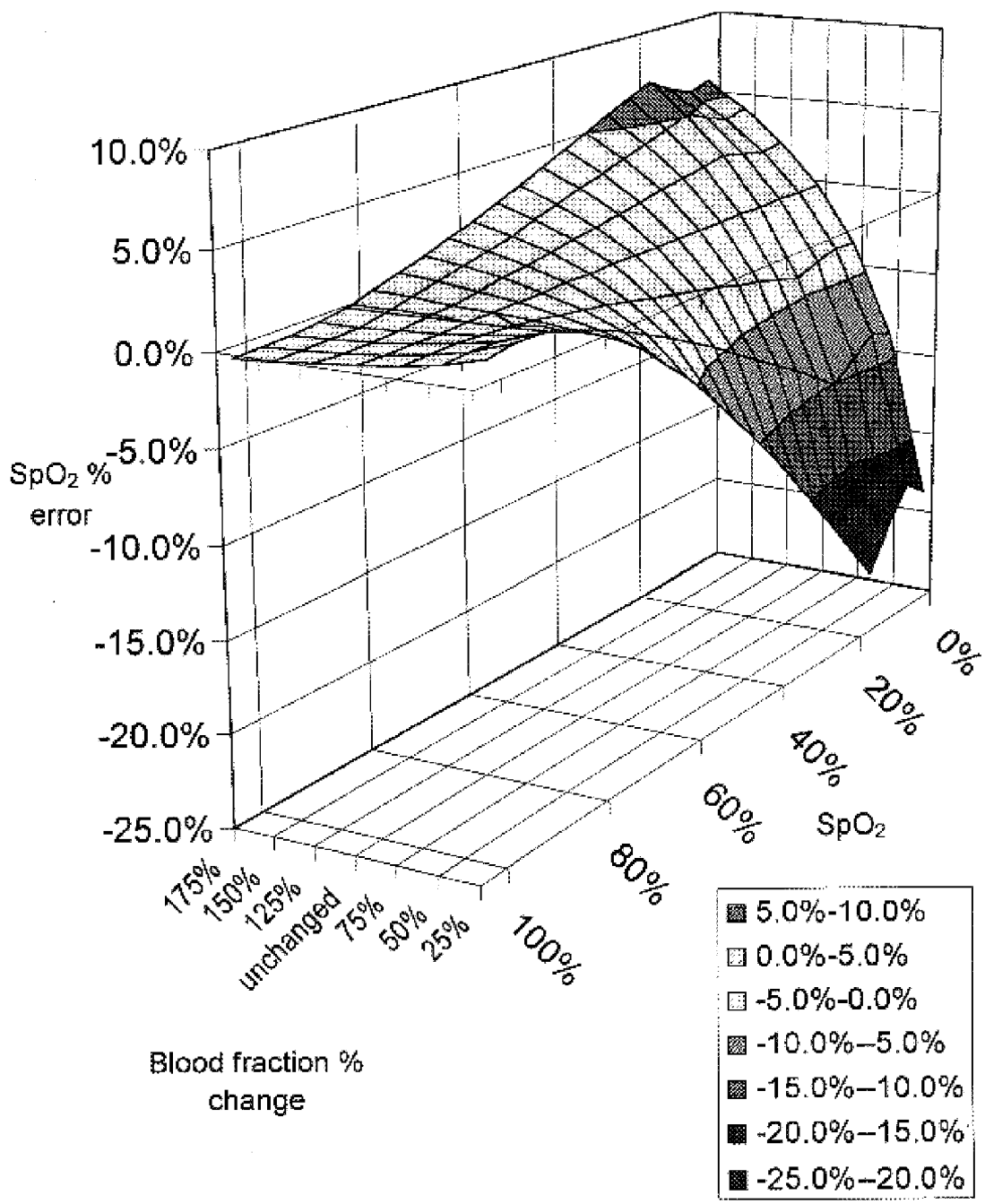
FIG. 8 is a graph relating the predicted error in $SpO_2$ to blood fraction and $SpO_2$, corresponding to the calibration surface of FIG. 7.

As an example of the result of perturbing a model parameter, the effect of blood fraction variation on calibration is illustrated in FIG. 7. The path along the calibration surface for the "unchanged" (or normal) blood fraction value corresponds to the curve shown in FIG. 6. As the blood fraction is reduced, the calibration curve becomes steeper. One way to assess the impact of this upon pulse oximetry accuracy is to graph the difference between the correct oxygen saturation value and the $SpO_2$ value obtained by assuming the nominal calibration for the nominal, "unchanged" blood fraction when the blood fraction is actually perturbed. In other word $$\text{error}(SpO_2) = SpO_2^{true} - SpO_2^{perturbed} \quad (3)$$

where all $SpO_2$ values here are percentages, and $SpO_2^{perturbed}$ is the $SpO_2$ value calculated with FIG. 6 calibration. The $SpO_2$ error surface is illustrated in FIG. 8, corresponding to the calibration surface of FIG. 7. It is apparent that reduction of the blood fraction to 25% of the nominal calibration value could result in a dramatic underestimation of the $SpO_2$ value at lower oxygen saturations; the error surface of FIG. 8 shows a maximum estimated error of −20% to −25% for the 25% blood fraction change. An increase in blood fraction could result in an overestimation of the $SpO_2$ value, albeit a much smaller magnitude; the error surface of FIG. 8 shows an estimated error of >5% but less than 10%.

In a similar fashion, calibration and error surfaces may be obtained for other scenarios, such as a change in the relative fraction of arterial versus venous blood; hematocrit reduction (anemia); or hematocrit increase (polycythemia). All of these scenarios are hereafter referred to as "non-ideal" tissue site characteristics. It is noted that the perturbed values are considered "non-ideal" only because they differ from assumptions at the time of calibration. Such differences may or may not be clinically significant for physiological reasons. The simplifications built into this model, such as homogeneity of the tissue, should always be considered when applying the results. Selection of an appropriate tissue site for monitoring can affect the applicability of the model, especially if the structure of the site invalidates the model's assumption of uniform penetration of light. However, as will be seen, use of a different or more advanced model of light behavior in tissue does not detract from the applicability of the invention. Further, the method applies to emitter-detector spacing variation (as may occur in transmissive mode sensor geometry).

The cited prior art reveals that the choice of wavelengths of light used for pulse oximetry influences the nature and magnitude of errors resulting from non-ideal tissue site characteristics. The model based on equations (1)–(2) predicts that different wavelengths of light may result in different calibration deviations for the same non-ideal tissue site characteristic. The present invention makes use of this effect to facilitate stabilization of the calibration with respect to a range of non-ideality in a particular tissue site characteristic.

For stabilizing deviations in the concentration of hemoglobin in blood, the total blood fraction, or the relative proportions of arterial and venous blood, it is sufficient to note that the dependency on blood fraction lies in the light attenuation factor $\alpha_\lambda$, found in the denominator of the factor $K_\lambda$. Since either the normalized pulse amplitudes $N_\lambda$ or the resulting ratio R (equation 1) are quantities calculated in typical pulse oximetry systems, in a preferred embodiment correction function(s) are defined for either the $N_\lambda$ or R:

$$N_r' = C_r(\{N_\lambda\}) \quad (4)$$

$$N_{ir}' = C_{ir}(\{N_\lambda\}) \quad (5)$$

or $$R' = C(\{N_\lambda\}) \quad (6)$$

where

| | |
|---|---|
| $N_\lambda$ | observed normalized pulse amplitude, wavelength λ |
| $N_\lambda'$ | corrected normalized pulse amplitude, wavelength λ |
| R' | corrected value of ratio R |
| $C_\lambda(\ )$ | correction function for wavelength λ |
| $C(\ )$ | correction function for ratio R. |

The wavelength correction functions $C_\lambda(\ )$ and the ratio correction function $C(\ )$ are alternative approaches to obtaining a calibration deviation correction. Each correction function $C_\lambda(\ )$ for a wavelength λ computes the corrected normalized pulse amplitude $N_\lambda'$ for one wavelength λ, from the set of (possibly perturbed) normalized pulse amplitudes measured by the oximeter, $\{N_\lambda\}$ 27. The correction function $C(\ )$ for ratio R takes the same $\{N_\lambda\}$ but computes the corrected ratio R'. The forms shown are generic, and not all $\{N_\lambda\}$ may be required for a particular correction function. Note that $N_\lambda$ in equations (4), (5) and (6) is analogous to the $n_\lambda$ of equations (1)–(2). It is noted that correction function(s) may be applied to the input signals themselves, other derivations thereof, or even their electrical counterparts prior to digitization without departing from the invention in its broadest aspects.

In any model sophisticated enough to illustrate the deviations in calibration resulting from non-ideal tissue site characteristics, the interaction of the parameters such as absorption and scattering coefficients, hematocrit, arterial and venous blood fraction, and sensor geometry is complex. A particular implementation of correction functions will likely work better over some part of the oxygen saturation range, hereinafter referred to as the "range of application", and be unnecessary over another part of the oxygen saturation range. In the example illustrated above, the need for correction is minimal at 70% oxygen saturation and above as shown in FIG. 8, so the range of application might be less than 70% oxygen saturation.

The correction functions $C_\lambda(\ )$, $C(\ )$ may be obtained in a number of different ways. An analytical solution may be derived, based upon the particular details and assumptions of the model being used. Substituting in an expression for the perturbed model parameter in terms of a deviation (multiplier or additive factor) and the original parameter value, the equations (4), (5) and (6) may be rearranged into a function yielding a corrected $N_\lambda'$ for one wavelength in terms of the set $\{N_\lambda\}$, or a corrected R'. The analytical solution may not result in a computationally acceptable equation, depending upon the mathematical model and the constraints imposed by the hardware configuration of the pulse oximeter. Another drawback of the approach is that its robustness is limited to that of the model in use.

Numerical solutions for the correction functions $C_\lambda(\ )$, $C(\ )$ are readily obtained, and the form of the solution (choice of mathematical operations, etc.) may be tailored to the hardware configuration of the pulse oximeter. A general form is chosen (e.g., linear versus exponential), and a curve fit procedure applied to a data set consisting of samples of $\{N_\lambda\}$ measured over the range of oxygen saturation and while varying the perturbation of the tissue site characteristic to be stabilized. Each sample of $\{N_\lambda\}$ is collected under a particular degree and type of non-ideality in the tissue site characteristic, spanning the range of practical interest.

The samples of $\{N_\lambda\}$ may consist of empirical data collected from laboratory studies while varying both oxygen saturation and the perturbed tissue site characteristic, or results predicted by the same (or an alternative) mathematical model under conditions of perturbation. For either way of collecting samples of {$N_\lambda$}, $SaO_2$, the true oxygen saturation level at the time of the sample, must be known by an independent means in empirical studies, such as, arterial blood gas analysis. Conditions should remain stable long enough to collect a representative sample of pulses (e.g., a dozen cardiac cycles). Note that it is unnecessary to quantify the perturbed parameter exactly; it is sufficient to know that the range of perturbation to be corrected has been spanned. Corresponding to the example above, hypoxia would be induced in a laboratory model with the blood fraction modified e.g., by inducing anemia, surgically reducing arterial blood flow to the tissue site, etc.

Use of empirical data offers the advantage of capturing representative behavior that may be beyond the scope of a mathematical model. Aside from the technical difficulties of such laboratory work, however, the resulting correction functions $C_\lambda(\ )$, $C(\ )$ will only be as reliable as the laboratory model used to represent the actual clinical condition(s) that will be encountered. Ideally, correction functions $C_\lambda(\ )$, $C(\ )$ obtained from empirical data should be validated against functions $C_\lambda(\ )$, $C(\ )$ derived either analytically or numerically from the model of light behavior (in the example, photon diffusion theory) under the same simulated perturbation.

The data employed to derive the correction function(s) $C_\lambda(\ )$, $C(\ )$ need not be uniformly distributed over either the oxygen saturation or the perturbed parameter range. By weighting data in the range of application more heavily, the algorithm employed to derive the correction function(s) $C_\lambda(\ )$, $C(\ )$ may be biased to reduce the likelihood of error where it is least tolerated.

It will be noted that other mathematical methods can be employed to derive solutions for the correction functions $C_\lambda(\ )$, $C(\ )$, including adaptive neural networks, genetic optimization algorithms, etc., without departing from the invention in its broadest aspects.

To illustrate the efficacy of the calibration stabilization approach, correction functions $C_\lambda(\ )$, $C(\ )$ were derived numerically from the results predicted by the model of equations (1)–(2) under the same range of blood fraction variation shown in FIGS. 7–8. The minimal number of wavelengths required for a pulse oximeter employing the disclosed means of calibration stabilization for some non-ideal tissue site characteristic is three, but more wavelengths may be incorporated. For example, in the case of blood fraction variation, a red wavelength of 690 nm results in a calibration and error surface similar to those shown in FIGS. 7–8 for 660 nm, but with an overall lower magnitude of red/infrared ratios and error magnitudes. Thus $\lambda \in \{660, 690, 890\}$, the correction wavelength set is the set of all three wavelengths, and the ratio wavelength set is $\{660, 890\}$.

Two correction functions, $C_{660}(\ )$ and $C_{890}(\ )$, were derived, employing the LINEST linear estimation algorithm of Microsoft(® Excel 2000, run on a data set over the blood fraction range of 25% to 175% and the oxygen saturation range of 0% to 100%. The parameters to the estimation algorithm were $N_{660}$, $N_{690}$, $N_{890}$, $1/N_{660}$, $1/N_{690}$, and $1/N_{890}$ calculated for each sample. The resulting correction functions for the normalized pulse amplitudes are $$C_{660}(N\lambda)=14.376-3.33568N_{660}+4.805N_{690}+0.2263N_{890}+179.25/N_{660}-350.47/N_{690}+405.6/N_{890} \quad (7)$$

and $$C_{890}(N\lambda)-21.614+0.6293N_{660}-0.89385N_{690}-0.089587N_{890}-3.8/N_{660}+10.0548/N_{690}-58.4225/N_{890} \quad (8)$$

Figure 9:
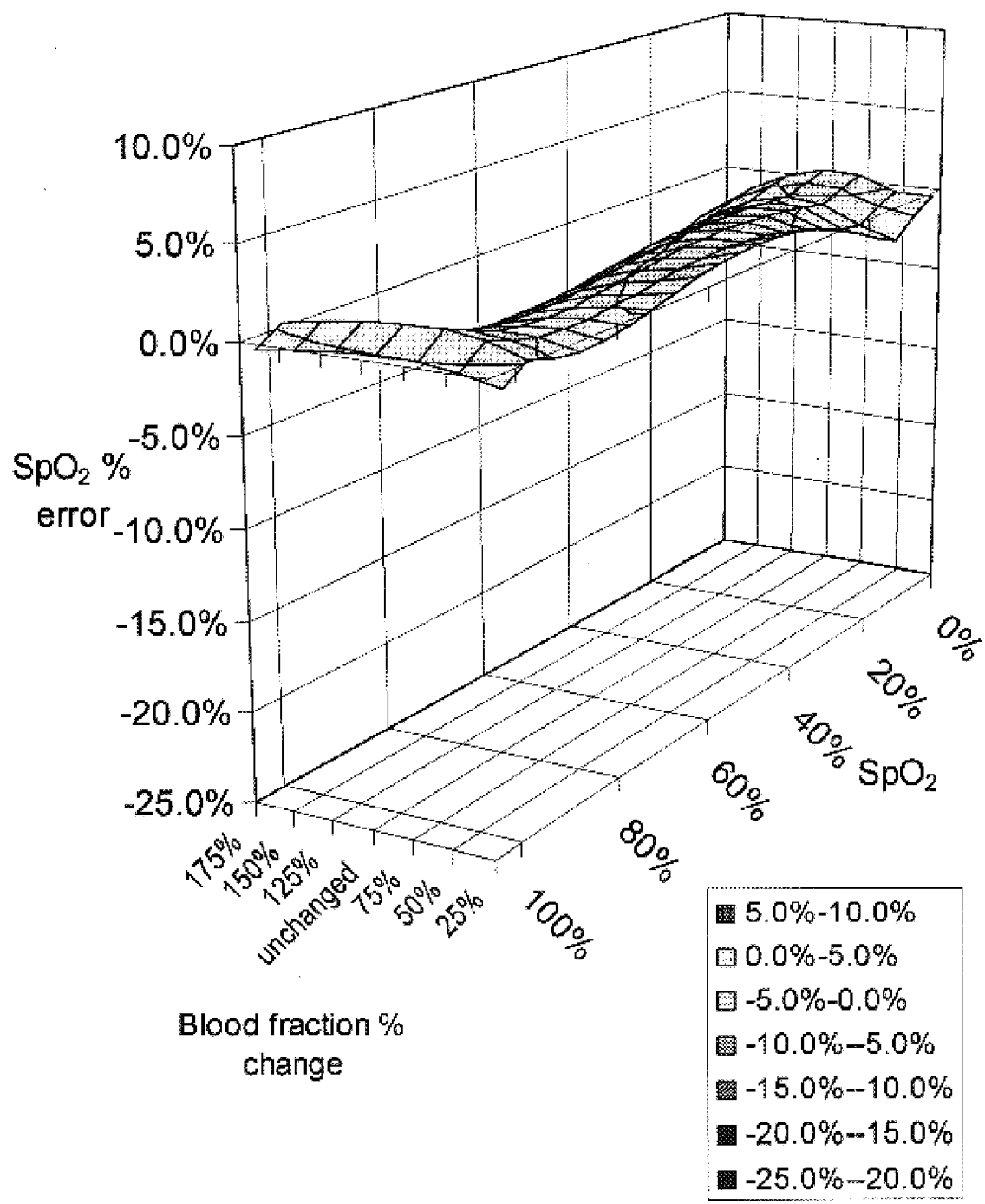
FIG. 9 is a graph relating the predicted error in $SpO_2$ to blood fraction and $SpO_2$, after calibration stabilization as taught in the invention.

The calibration deviation corrections obtained from these functions are in the form of the corrected $N_{660}'$ and $N_{890}'$ values, which are in turn utilized to calculate the corrected ratio R'. The $SpO_2$ error surface resulting from use of the corrected $N_{660}'$ and $N_{890}'$ is shown in FIG. 9. In comparison to FIG. 8, advantageously predicted error is now well within 5% (−4.7% to +1.2%) across the entire range of oxygen saturation and blood fraction perturbation, with the average error only −0.9%.

A ratio correction function $C(\ )$ was also derived; under the same conditions of blood fraction variation. The parameters to the estimation algorithm were $N_{660}/N_{890}$, $N_{690}/N_{890}$, and $N_{660}/N_{690}$, calculated for each combination of oxygen saturation and blood fraction perturbation in the data set. The first two parameters are the R values calculated for 660 nm versus 890 nm, and 690 nm versus 890 nm, which hereafter will be designated as $R_{660}$ and $R_{690}$, respectively. The third parameter is the ratio of normalized pulse amplitudes for 660 nm and 690 nm. The resulting correction function for the red/infrared ratio is $$C(N\lambda)=-2.02-3.858R_{660}+6.005R_{690}+1.477(N_{660}/N_{690}) \quad (9)$$

Figure 10:
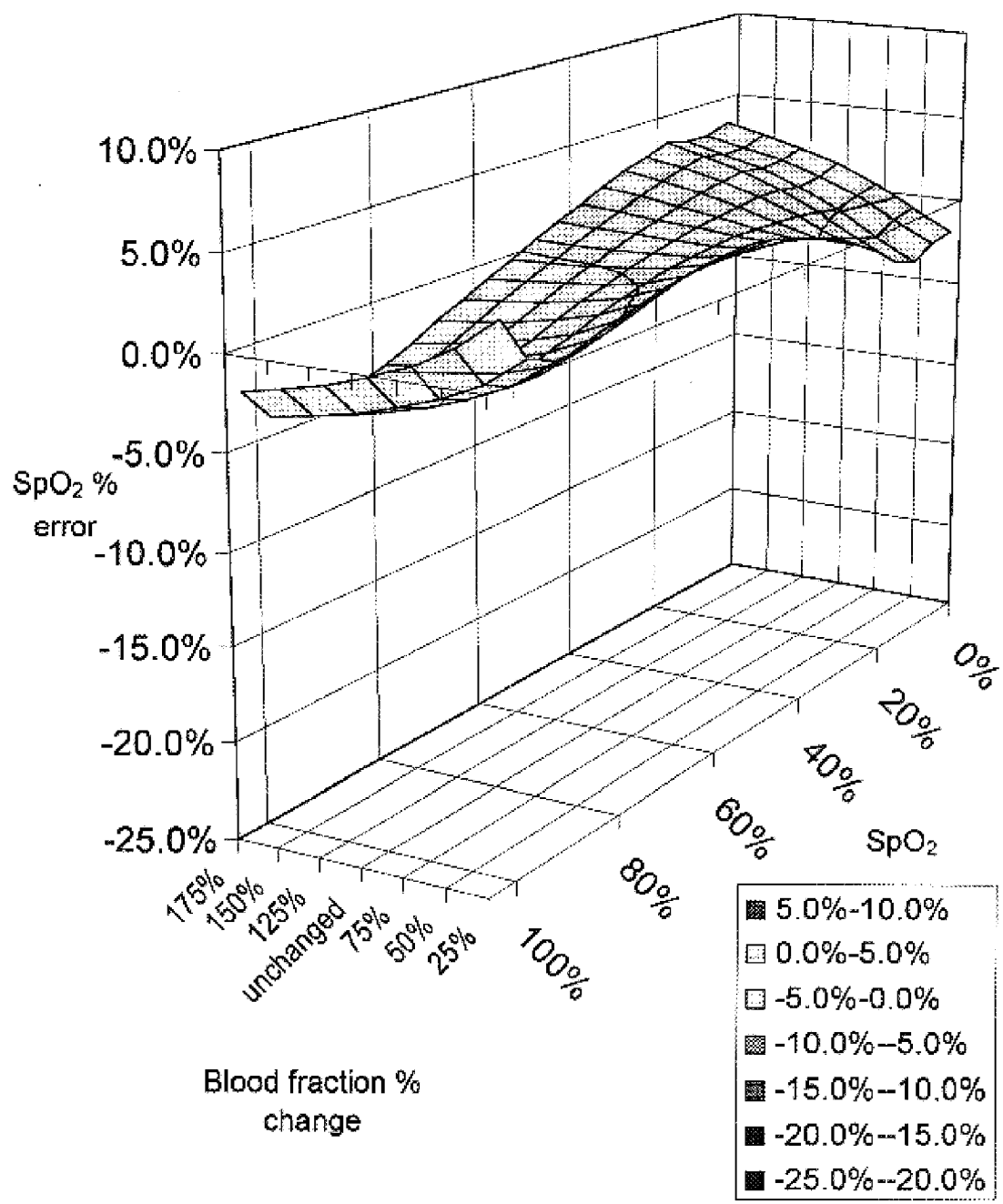
FIG. 10 is a graph relating the predicted error in $SpO_2$ to blood fraction and $SpO_2$, after another calibration stabilization as taught in the invention.

The calibration deviation correction obtained from function $C(N_\lambda)$ is in the form of a corrected ratio value, R'. The $SpO_2$ error surface resulting from use of the corrected ratio is shown in FIG. 10. Again, the magnitude of the predicted error is well within 5% (−4.6% to +3.4%) across the entire range of oxygen saturation and blood fraction perturbation, with the average error only −0.2%.

The general form used in the correction functions above, a sum of simple factors, was chosen to illustrate a computationally inexpensive solution to a calibration deviation problem already discussed in the prior art. Alternatively higher order polynomials, logarithmic or exponential functions, and other transformations may be used in these functions without changing the overall intent of the invention. Furthermore, the correction functions can be derived by any of a variety of curve fit and minimization methods, including genetic optimization algorithms and neural networks.

An extension of the invention includes use of sets of correction function(s) for multiple non-ideal tissue site characteristics. A choice of which set of correction function(s) to apply is based upon information about the application (e.g., fetal versus adult versus neonatal monitoring), the mode of operation (transmissive versus reflectance), the monitoring site (e.g., finger versus earlobe), as well as a priori medical information (e.g., presence of anemia or blood loss).

Although the correction functions are shown as procedural steps in the software embedded in the computing component 14 of pulse oximeter 100, part or all of the calculations may be performed a priori and the results stored in look-up table form in the memory storage component 15 without departing from the invention in its broadest aspects.

WAVELENGTH SELECTION

The present invention relies on the proper selection of wavelengths of light to reduce the calibration deviation, explained supra. This section reveals means of selecting wavelengths for use in the invention. Table I contains normalized pulse amplitude ($N_\lambda$) data for selected oxygen saturation ($SpO_2\%$) and selected blood fraction levels, as predicted by the Schmitt's photon diffusion model discussed supra, for certain wavelengths $\lambda$ of interest. "Normal" in the "Fraction (%)" column refers to the "unchanged" lines in FIGS. 7–10.

TABLE I

| Blood Fraction (%) | λ (nm) | $N_\lambda$ $SpO_2 = 0\%$ | $N_\lambda$ $SpO_2 = 20\%$ | $N_\lambda$ $SpO_2 = 40\%$ | $N_\lambda$ $SPO_2 = 100\%$ |
|---|---|---|---|---|---|
| normal | 660 | 39.0 | 33.5 | 28.5 | 5.5 |
| 25% |  | 63.8 | 53.8 | 44.1 | 6.8 |
| normal | 690 | 31.9 | 27.5 | 23.5 | 6.4 |
| 25% |  | 50.3 | 42.6 | 35.2 | 7.8 |
| normal | 735 | 19.4 | 17.2 | 15.1 | 7.6 |
| 25% |  | 27.8 | 24.3 | 20.8 | 9.3 |
| normal | 805 | 12.6 | 12.6 | 12.6 | 12.7 |
| 25% |  | 16.6 | 16.6 | 16.7 | 16.8 |
| normal | 890 | 11.9 | 12.7 | 13.3 | 15.1 |
| 25% |  | 16.0 | 17.2 | 18.2 | 21.3 |

The wavelengths employed in the sensor 10 must satisfy requirements for (1) detected light intensity in, reflectance mode operation, (2) normalized pulse amplitude, (3) sensitivity to oxygen saturation change, and (4) differential sensitivity to the non-ideal tissue site characteristic(s) of concern. The practical concern is that the signals obtained at the chosen wavelengths λ exhibit sufficient amplitude variation over the range of both oxygen saturation and tissue site characteristic(s).

The first requirement, detected light intensity, is met by choosing wavelengths ) in the broad range of 600–1000 nm. As shown in FIG. 5, the absorption of light by both oxygenated and reduced hemoglobin rises sharply below about 670 nm, making it difficult to guarantee a sufficiently large detected signal from shorter wavelengths without unacceptably high power levels. All the wavelengths considered in the present invention provide adequate detected light intensity.

The normalized pulse amplitude $N_\lambda$ at a particular wavelength λ gives a relative indication of how reliably pulse amplitudes can be measured. Referring to Table I, the red wavelengths (λ<800 nm) all have large pulse amplitudes $N_\lambda$ at low oxygen saturations ($SpO_2$=0%, 20% or 40%), with 660 nm providing the largest pulsatile signal in that range, followed by 690 nm and 735 nm. At high oxygen saturations ($SpO_2$=100%), the $N_\lambda$ are quite small, especially for all the shorter wavelengths (λ<800 nm); however, most prior art pulse oximeters cope adequately with this reality. It is noted that the 805 nm wavelength is essentially insensitive to oxygen saturation ($N_{805}$ is unchanged across the $SpO_2$ range from 0% to 100% for a given Blood Fraction (%)), representing an isobestic point in absorbance for oxygenated and reduced hemoglobin forms.

The sensitivity S of a given red/infrared wavelength combination to oxygen saturation variation, can be measured as the slope of the calibration curve, or approximately $$S_{100} = \Delta R/\Delta SpO_2 \approx R^{0\%} - R^{100\%} \quad (10)$$

where $S_{100}$ is the sensitivity over the range of $SpO_2$ from 0% to 100% and R is the red/IR ratio shown in the calibration curve of FIG. 6 and the calibration surface in FIG. 7. $R^{0\%}$ is the ratio R at $SpO_2$=0% and $R^{100\%}$ is the ratio R at $SpO_2$=100%.

The larger the $S_{100}$ value, the better the pulse oximeter will be able to overcome noise in the signals. The data in Table I can be used to derive the values of $S_{100}$ for normal and reduced blood fraction, taking the ratio R between different wavelength combinations, as shown in Table II.

TABLE II

| Blood Fraction (%) | λ (nm) | $S_{100}$ 660 | $S_{100}$ 690 | $S_{100}$ 735 | $S_{100}$ 805 |
|---|---|---|---|---|---|
| normal | 690 | 0.35702 |  |  |  |
| 25% |  | 0.40158 |  |  |  |
| normal | 735 | 1.28070 |  |  |  |
| 25% |  | 1.56212 |  |  |  |
| normal | 805 | 2.67657 |  |  |  |
| 25% |  | 3.44568 |  |  |  |
| normal | 890 | 2.91094 | 2.25348 | 1.12776 | 0.21109 |
| 25% |  | 3.66683 | 2.77390 | 1.30330 | 0.24377 |

For example, under conditions of normal blood fraction, the combination of 660 nm red and 890 nm infrared yields an $S_{100}$ of 2.91, and 690 nm combined with 890 nm yields an $S_{100}$ of 2.25. By comparison, the combination of 735 nm red and 890 nm infrared yields an $S_{100}$ of 1.13 under conditions of normal blood fraction.

It is often desirable to focus on a narrower range of the oxygen saturation parameter range for a particular application, where clinical decision-making demands minimization of the potential for error. The narrower range of the oxygen saturation parameter range is herein referred to as the critical range for operation, over the oxygen saturation interval [αβ] where (α<β). The critical range sensitivity $S_{cr}$ is the slope in the critical range for operation of the calibration curve over the oxygen saturation interval [αβ], or approximately $$S_{cr} \approx (R^\alpha - R^\beta)\frac{100}{(\beta - \alpha)} \quad (11)$$

As with $S_{100}$, the larger the $S_{cr}$, the better the pulse oximeter is able to overcome noise in the signals.

The last term in the expression of equation (11) scales the result by the critical range size, making $S_{cr}$ numerically comparable to $S_{100}$. In fetal pulse oximetry, it is generally agreed that $SpO_2$ readings above 40% are reassuring, readings below that level merit concern, and readings remaining below 30% are ominous. Hence a useful measure could be based upon [αβ]=[20% 40%]. The resulting critical range 61 for 20% oxygen saturation (20% $SpO_2$) to 40% oxygen saturation (40% $SpO_2$) is illustrated superimposed upon the calibration curve in FIG. 6.

Using the data of Table I, the values of $S_{cr}$ over the critical range of 20–40% are computed for different wavelength ratios, as shown in Table III. (The non-zero lower limit on the critical range is meant to imply that such low values are treated as ominous with a high degree of certainty, not that accuracy is unnecessary.)

TABLE III

| Blood Fraction (%) | λ (nm) | $S_{cr}$ 660 | $S_{cr}$ 690 | $S_{cr}$ 735 | $S_{cr}$ 805 |
|---|---|---|---|---|---|
| normal | 690 | 0.03536 |  |  |  |
| 25% |  | 0.04335 |  |  |  |
| normal | 735 | 0.34815 |  |  |  |
| 25% |  | 0.48184 |  |  |  |
| normal | 805 | 2.03402 |  |  |  |
| 25% |  | 2.93867 |  |  |  |

TABLE III-continued

| Blood Fraction (%) | λ (nm) | $S_{cr}$ 660 | 690 | 735 | 805 |
|---|---|---|---|---|---|
| normal | 890 | 2.52551 | 2.02152 | 1.09275 | 0.22438 |
| 25% | | 3.55630 | 2.75169 | 1.35741 | 0.26716 |

Under conditions of normal blood fraction, the combination of 660 nm red and 890 nm infrared yields an $S_{cr}$ of 2.526, and 690 nm red combined with 890 nm infrared yields an $S_{cr}$ of 2.022. By comparison under the conditions of normal blood fraction, the combination of 735 nm red and 890 nm infrared yields an $S_{cr}$ of 1.093.

The last requirement, differential sensitivity to the non-ideal tissue site characteristics of concern, is satisfied as follows. The suitability of useful wavelengths for correcting calibration deviation due to perturbation of a particular tissue site characteristic is assessed in two steps. First, there must be an adequate pulsatile signal to yield normalized pulse amplitudes $N_\lambda$. As previously discussed, this is assessed by comparing the $N_\lambda$. Assuming this is true, then secondly the differential sensitivity of a pair of wavelengths, e.g., $\mu$ and v, must be sufficient to be of practical use in calculating corrected $N_\lambda$. Again defining both full-range differential sensitivity $D_{100}$ and critical range differential sensitivity $D_{cr}$ measures gives $$D_{100} = (S_{100,\mu:v}^{pert} - S_{100,\mu:v}^{norm})/S_{100,\mu:v}^{norm} \quad (12)$$

and $$D_{cr} = (S_{cr,\mu:v}^{pert} - S_{cr,\mu:v}^{norm})/S_{cr,\mu:v}^{norm} \quad (13)$$

where $S_{100,\mu:v}$ and $S_{cr,\mu:v}$ are the sensitivity for wavelength combination $\{\mu, v\}$, taken respectively over the entire range and just the critical range $[\alpha\beta]$ (where $\alpha<\beta$).

Each differential sensitivity is the normalized difference in slope of a line approximating the calibration curve between normal ("norm") and perturbed ("pert") conditions, for two wavelengths $\mu$ and v of the correction wavelength set, over either the entire oxygen saturation range or just the critical range.

Comparing the rows labeled "normal" blood fraction with those labeled "25%" (reduced) blood fraction as the perturbed case, the $D_{100}$ and $D_{cr}$ values may be calculated from Tables II and III, respectively for critical range 20–40%. Since detection and elimination of perturbation requires differential sensitivity to calibration deviation, all of the available wavelengths should be combined pairwise. The values for differential sensitivity to variation in blood fraction from normal to 25% of normal are presented in Table IV.

TABLE IV

| $SpO_2$ range | λ (nm) | 660 | 690 | 735 | 805 |
|---|---|---|---|---|---|
| $D_{100}$ | 690 | 0.12481 | | | |
| $D_{cr}$ | | 0.22596 | | | |
| $D_{100}$ | 735 | 0.21974 | | | |
| $D_{cr}$ | | 0.38400 | | | |
| $D_{100}$ | 805 | 0.28735 | | | |
| $D_{cr}$ | | 0.44476 | | | |
| $D_{100}$ | 890 | 0.25967 | 0.23094 | 0.15565 | 0.15482 |
| $D_{cr}$ | | 0.40815 | 0.36120 | 0.24220 | 0.19066 |

It is noted that the differential sensitivity to blood fraction reduction in the critical range $D_{cr}$ is greater than differential sensitivity over the full range $D_{100}$ in all cases. Since the critical range represents the lower portion of the oxygen saturation range, it is consistent with the model of the present invention that addition of the higher saturation range would result in diminished overall sensitivity to blood fraction change (see FIG. 7).

The differential sensitivity to blood fraction in the critical range $D_{cr}$ can identify wavelength combinations that are relatively insensitive to blood fraction perturbation for use in conventional, two-wavelength sensors. Thus, {735, 890} has a low $D_{cr}$ of 0.24220, but this and other low-$D_{cr}$ combinations such as {660, 690} and {805, 890} are also less sensitive to oxygen saturation.

Wavelengths with the largest $D_{cr}$ values should result in the best sensitivity for perturbation, giving the strongest input for the correction functions when added to the correction wavelength set. This includes {660, 805} with a $D_{cr}$ of 0.44476, {660, 735} with a $D_{cr}$ 0.38400, and {690, 890} with $D_{cr}$ 0.36120.

Based upon the oxygen sensitivity $S_{100}$, $S_{cr}$ and differential sensitivity, $D_{100}$, $D_{cr}$ calculations, the preferred embodiment utilizes a ratio wavelength set of {660, 890} for oxygen saturation calculation, preferably adding the 805 nm isobestic wavelength to accomplish correction. This is intuitively attractive, since the added wavelength is insensitive to oxygen saturation. However, the other wavelengths suggested e.g. 690 nm, 735 nm are also sufficient to correct the calibration deviation resulting from a large blood fraction reduction, and may be preferred for other reasons. For example, 690 nm produces large, and hence easily resolved, pulse amplitudes at low saturations, and 735 nm may be useful as revealed in the prior art because in combination with infrared wavelengths it is relatively insensitive to blood fraction variation. Another consideration in choice of wavelength is the cost and availability of light sources at various wavelengths. If data acquisition and processing components of the device can provide adequate resolution of the signals to yield usable normalized pulse amplitudes, any of the additional wavelengths can suffice.

The reduction in blood fraction has been chosen to illustrate the preferred embodiment of the invention, because as noted above the perturbation resulting from reduction in blood fraction far exceeds that resulting from a blood fraction increase (see FIG. 8). However, the same approach for assessing differential sensitivity $D_{100}$, $D_{cr}$ to perturbation can be applied to other tissue characteristics.

Although an exemplary embodiment of the present invention has been shown and described with reference to particular embodiments and applications thereof, it will be apparent to those having ordinary skill in the art that a number of changes, modifications, or alterations to the invention as described herein may be made, none of which depart from the spirit or scope of the present invention. All such changes, modifications, and alterations should therefore be seen as being within the scope of the present invention and that the scope of the present invention be limited solely by the broadest interpretation that lawfully can be accorded in the appended claims.

I claim:

1. A method for determining oxygen saturation in a pulse oximeter having a calibration stabilization process for reducing a deviation in calibration comprising the following steps:

exposing a tissue site to a plurality of wavelengths of light generated by the pulse oximeter;

defining a tissue site characteristic, other than oxygen saturation, which may influence the determination of oxygen saturation;

defining a ratio wavelength set as a first subset of the plurality of wavelengths for calculation of an oxygen saturation value;

defining a correction wavelength set as a second subset of the plurality of wavelengths for detection and correction of a deviation in the calibration of the oxygen saturation calculation over a specified range of oxygen saturation, due to a perturbation of the tissue site characteristic, and including selecting the correction wavelength set to optimize the correction of the deviations;

detecting light of the plurality of wavelengths transmitted by or reflected from components of the tissue site and converting the detected light into a plurality of electrical signals;

digitizing and conditioning the plurality of electrical signals in a signal data acquisition component of the pulse oximeter to yield a plurality of input signals;

defining a set of correction function(s) operating upon the plurality of input signals and substantially removing deviations from the input signals corresponding to the ratio wavelength set;

calculating a plurality of normalized pulse amplitudes from the plurality of input signals in a processing component of the pulse oximeter;

detecting the deviation in input signals corresponding to the correction wavelength set, and if the deviation is present calculating a calibration deviation correction by applying the set of correction function(s) to the input signals corresponding to the correction wavelength set, and;

calculating an oxygen saturation value from a ratio of normalized pulse amplitudes corresponding to the ratio wavelength set, and utilizing the calibration deviation correction.

2. The method as defined in claim 1, wherein the tissue site characteristic is a fraction of blood in the tissue.

3. The method as defined in claim 1, wherein the tissue site characteristic is a hematocrit of blood in the tissue.

4. The method as defined in claim 1, wherein the tissue site characteristic is a relative proportion of arterial to venous blood in the tissue.

5. The method as defined in claim 1, wherein the specified range of oxygen saturation is 0–100%.

6. The method as defined in claim 1, wherein the specified range of oxygen saturation is 0–70%.

7. The method as defined in claim 1, wherein the specified range of oxygen saturation is 20–40%.

8. The method as defined in claim 1, wherein the selecting the correction wavelength set to optimize the correction of the deviation is based upon a differential sensitivity of a pair of wavelengths from the correction wavelength set to a perturbation of the tissue site characteristic, and the differential sensitivity is calculated as a change in slope of a ratio resulting from perturbation, nornmalized by a value of an unperturbed slope.

9. The method as defined in claim 1, wherein the ratio wavelength set consists of a red wavelength in the range of 650–699 nm, and an infrared wavelength in the range of 850–950 nm.

10. The method as defined in claim 1, wherein the correction wavelength set consists of one or more wavelength(s) of the ratio wavelength set, and another different red wavelength in the range of 650–699 nm.

11. The method as defined in claim 1, wherein the correction wavelength set consists of one or more wavelengths of the ratio wavelength set, and another wavelength, which is near an isobestic point of oxygenated versus reduced hemoglobin absorption, and found in the range of 800–815 nm.

12. The method as defined in claim 1, wherein the correction wavelength set consists of one or more wavelengths of the ratio wavelength set, and another wavelength in the range of 700–799 nm.

13. The method as defined in claim 1, wherein one set of correction function(s) among a plurality of sets of correction function(s) corresponding to a plurality of tissue site characteristic perturbations is chosen for use with the plurality of normalized pulse amplitudes.

14. The method as defined in claim 1, wherein the tissue site is located on a fetus in utero.

15. A method for determining oxygen saturation in a pulse oximeter having a calibration stabilization process for reducing a deviation in calibration comprising the following steps:

exposing a tissue site to a plurality of wavelengths of light generated by the pulse oximeter;

defining a tissue site characteristic, other than oxygen saturation, which may influence the determination of oxygen saturation;

defining a ratio wavelength set as a first subset of the plurality of wavelengths for calculation of an oxygen saturation value, including selecting the ratio wavelength set to optimize oxygen saturation sensitivity over a specified range;

defining a correction wavelength set as a second subset of the plurality of wavelengths for detection and correction of a deviation in the calibration of the oxygen saturation calculation over a specified range of oxygen saturation, due to a perturbation of the tissue site characteristic;

detecting light of the plurality of wavelengths transmitted by or reflected from components of the tissue site and converting the detected light into a plurality of electrical signals;

digitizing and conditioning the plurality of electrical signals in a signal data acquisition component of the pulse oximeter to yield a plurality of input signals;

defining a set of correction functions operating upon the plurality of input signals and substantially removing deviations from the input signals corresponding to the ratio wavelength set;

calculating a plurality of normalized pulse amplitudes from the plurality of input signals in a processing component of the pulse oximeter;

detecting the deviation in input signals corresponding to the correction wavelength set, and if the deviation is present calculating a calibration deviation correction by applying the set of correction functions to the input signals corresponding to the correction wavelength set, and;

calculating an oxygen saturation value from a ratio of normalized pulse amplitudes corresponding to the ratio wavelength set, and utilizing the calibration deviation correction.

16. The method as defined in claim 15, wherein the step of defining a ratio wavelength set includes determining a slope of a calibration curve of the ratio of the normalized pulse amplitudes versus oxygen saturation, the calibration curve corresponding to a pair of wavelengths from the ratio wavelength set; and basing the selecting to optimize oxygen saturation sensitivity over the specified range upon maximizing the magnitude of a slope over the specified range of oxygen saturation.

17. A method for determining oxygen saturation in a pulse oximeter having a calibration stabilization process for reducing a deviation in calibration comprising the following steps:
   exposing a tissue site to a plurality of wavelengths of light generated by the pulse oximeter;
   defining a tissue site characteristic, other than oxygen saturation, which may influence the determination of oxygen saturation;
   defining a ratio wavelength set as a first subset of the plurality of wavelengths for calculation of an oxygen saturation value;
   defining a correction wavelength set as a second subset of the plurality of wavelengths for detection and correction of a deviation in the calibration of the oxygen saturation calculation over a specified range of oxygen saturation, due to a perturbation of the tissue site characteristic;
   detecting light of the plurality of wavelengths transmitted by or reflected from components of the tissue site and converting the detected light into a plurality of electrical signals;
   digitizing and conditioning the plurality of electrical signals in a signal data acquisition component of the pulse oximeter to yield a plurality of input signals;
   defining a set of correction function(s) operating upon the plurality of input signals and substantially removing deviations from the input signals corresponding to the ratio wavelength set;
   calculating a plurality of normalized pulse amplitudes from the plurality of input signals in a processing component of the pulse oximeter;
   detecting the deviation in input signals corresponding to the correction wavelength set, and if the deviation is present calculating a calibration deviation correction by applying the set of correction functions to the input signals corresponding to the correction wavelength set, wherein the calibration deviation correction obtained from each correction function(s) is a corrected normalized pulse amplitude computed from the plurality of input signals and;
   calculating an oxygen saturation value from a ratio of normalized pulse amplitudes corresponding to the ratio wavelength set, and utilizing the calibration deviation correction.

18. A method for determining oxygen saturation in a pulse oximeter having a calibration stabilization process for reducing a deviation in calibration comprising the following steps:
   exposing a tissue site to a plurality of wavelengths of light generated by the pulse oximeter;
   defining a tissue site characteristic, other than oxygen saturation which may influence the determination of oxygen saturation;
   defining a ratio wavelength set as a first subset of the plurality of wavelengths for calculation of an oxygen saturation value;
   defining a correction wavelength set as a second subset of the plurality of wavelengths for detection and correction of a deviation in the calibration of the oxygen saturation calculation over a specified range of oxygen saturation, due to a perturbation of the tissue site characteristic;
   detecting light of the plurality of wavelengths transmitted by or reflected from components of the tissue site and converting the detected light into a plurality of electrical signals;
   digitizing and conditioning the plurality of electrical signals in a signal data acquisition component of the pulse oximeter to yield a plurality of input signals;
   defining a set of correction function(s) operating upon the plurality of input signals and substantially removing deviations from the input signals corresponding to the ratio wavelength set;
   calculating a plurality of normalized pulse amplitudes from the plurality of input signals in a processing component of the pulse oximeter;
   detecting the deviation in input signals corresponding to the correction wavelength set, and if the deviation is present calculating a calibration deviation correction by applying the set of correction function(s) to the input signals corresponding to the correction wavelength set, wherein the calibration deviation correction obtained from the correction function is a corrected ratio of normalized pulse amplitudes computed from the plurality of input signals and;
   calculating an oxygen saturation value from a ratio of normalized pulse amplitudes corresponding to the ratio wavelength set, and utilizing the calibration deviation correction.

19. A method for determining oxygen saturation in a pulse oximeter having a calibration stabilization process for reducing a deviation in calibration comprising the following steps:
   exposing a tissue site to a plurality of wavelengths of light generated by the pulse oximeter;
   defining a tissue site characteristic, other than oxygen saturation, which may influence the determination of oxygen saturation;
   defining a ratio wavelength set as a first subset of the plurality of wavelengths for calculation of an oxygen saturation value;
   defining a correction wavelength set as a second subset of the plurality of wavelengths for detection and correction of a deviation in the calibration of the oxygen saturation calculation over a specified range of oxygen saturation, due to a perturbation of the tissue site characteristic;
   detecting light of the plurality of wavelengths transmitted by or reflected from components of the tissue site and converting the detected light into a plurality of electrical signals;
   digitizing and conditioning the plurality of electrical signals in a signal data acquisition component of the pulse oximeter to yield a plurality of input signals;
   defining a set of correction function(s) operating upon the plurality of input signals and substantially removing deviations from the input signals corresponding to the ratio wavelength set;
   calculating a plurality of normalized pulse amplitudes from the plurality of input signals in a processing component of the pulse oximeter;
   detecting the deviation in input signals corresponding to the correction wavelength set, including assessing an approximate oxygen saturation level calculated from an uncorrected normalized pulse amplitudes, and applying the correction function(s) only if the approximate oxygen saturation level is within a range of application for the correction function(s) and if the deviation is present calculating a calibration deviation correction by applying the set of correction function(s) to the input signals corresponding to the correction wavelength set, and;
   calculating an oxygen saturation value from a ratio of normalized pulse amplitudes corresponding to the ratio wavelength set, and utilizing the calibration deviation correction.

20. A pulse oximeter having a calibration stabilization process for reducing a deviation in calibration comprising:
a sensor device comprising light emitting device(s) and detector(s) placed against a tissue site;
a monitor device comprising at least a data acquisition component, a memory storage component, a visual presentation component, and a computing component having a capability for oxygen saturation determination with calibration stabilization for quantifying and/or correcting and/or eliminating a calibration deviation(s) resulting from changes in tissue site characteristics in a pulse oximetry signal, wherein the light emitting device(s) emit a plurality of wavelengths, the pulse oximeter utilizing in the computing component (a) a ratio wavelength set comprising at least one combination of the plurality of wavelengths, the one combination possessing high sensitivity to blood oxygen saturation changes, and (b) a correction wavelength set comprising at least two wavelengths, of which at least one of the two wavelengths is not already employed in the ratio wavelength set and which exhibits substantially different dependence upon a tissue site characteristic other than blood oxygen saturation.

21. The pulse oximeter as defined in claim 20, wherein the capability for, oxygen saturation determination with calibration stabilization includes:
defining a tissue site characteristic, other than oxygen saturation, which may influence the determination of oxygen saturation;
defining the ratio wavelength set as a first subset of a plurality of wavelengths for calculation of an oxygen saturation value;
defining the correction wavelength set as a second subset of the plurality of wavelengths for detection and correction of a deviation in the calibration of the oxygen saturation calculation over a specified range of oxygen saturation, due to a perturbation of the tissue site characteristic;
defining a set of correction function(s); and wherein the correction function(s) operate upon a plurality of input signals related to detected light received by the detector(s) and substantially remove deviations from the input signals corresponding to the ratio wavelength set; and
wherein the computing component calculates a plurality of normalized pulse amplitudes from the plurality of input signals and detects a deviation in an input signals corresponding to the correction wavelength set, and if the deviation is present calculates a calibration deviation correction by applying the set of correction function(s) to the input signals corresponding to the correction wavelength; and
calculates an oxygen saturation value from a ratio of normalized pulse amplitudes corresponding to the ratio wavelength set, utilizing the calibration deviation correction.

22. The pulse oximeter of claim 20, wherein the monitor device processes signal data acquired for each wavelength of the plurality of wavelengths in order to recalculate signals of the ratio wavelength set, based upon both a signal data of the ratio wavelength set, and a signal data of the correction wavelength set.

23. The pulse oximeter of claim 22, wherein the signal data of the ratio wavelength set and/or the signal data of the correction wavelength set are possibly perturbed.

24. The pulse oximeter as defined in claim 20, wherein the wavelengths of the light emitting device(s) of the sensor device are chosen so that a calibration deviation resulting from changes in more than one tissue site characteristic is quantified and/or corrected by employing more than one correction wavelength set.

25. The pulse oximeter as defined in claim 24, wherein the monitor device determines which correction wavelength set, if any, to employ in recalculating a signal data corresponding to the ratio wavelength set, based upon an estimate of a blood oxygen saturation level derived from the signal data corresponding to the ratio wavelength set.

26. The pulse oximeter as defined in claim 25, wherein the signal data corresponding to the ratio wavelength set is possibly perturbed.

27. The pulse oximeter as defined in claim 24, wherein the monitor device determines which correction wavelength set, if any, to employ in recalculating signal data corresponding to the ratio wavelength set, based upon a pattern of a magnitude(s) and a direction(s) of a deviation(s) in signal data corresponding to the correction wavelength set from an expected mathematical relationship(s) between a member(s) of each of the ratio wavelength set and the correction wavelength set.

28. The pulse oximeter system as defined in claim 20, wherein the sensor device is designed for intrauterine fetal pulse oximetry.

29. A calibration stabilization process for use in reducing calibration deviation in a pulse oximeter, the process comprising the steps of:
deriving a calibration surface and calibration error surface for a selected blood oxygen saturation range for a calibration deviation resulting from a change in a tissue site characteristics for a ratio wavelength set,
applying a correction function utilizing a correction wavelength set to operate on and remove the calibration deviation corresponding to the ratio wavelength set, wherein the correction function is a wavelength correction function; and
reducing the deviation across the blood oxygen saturation range for the change in the tissue site characteristics.

30. A calibration stabilization process for use in reducing calibration deviation in a pulse oximeter, the process comprising the steps of:
deriving a calibration surface and calibration error surface for a selected blood oxygen saturation range for a calibration deviation resulting from a change in a tissue site characteristics for a ratio wavelength set, wherein the ratio wavelength set possesses high sensitivity to blood oxygen saturation change;
applying a correction function utilizing a correction wavelength set to operate on and remove the calibration deviation corresponding to the ratio wavelength set, wherein the correction wavelength set includes at least two wavelengths, of which at least one wavelength is not in the ratio wavelength set and wherein the correction wavelength set exhibits different dependence upon the tissue site characteristics other than blood oxygen saturations;
and reducing the deviation across the blood oxygen saturation range for the change in the tissue site characteristics.

31. The calibration stabilization process as claimed in claim 30, wherein the oxygen saturation range is from 0% to 100%.

32. The calibration stabilization process as claimed in claim 30, wherein the correction function is a ratio correction function.

* * * * *